(12) United States Patent
Beasley et al.

(10) Patent No.: US 10,548,663 B2
(45) Date of Patent: Feb. 4, 2020

(54) NEUROMODULATION CATHETERS WITH SHAFTS FOR ENHANCED FLEXIBILITY AND CONTROL AND ASSOCIATED DEVICES, SYSTEMS, AND METHODS

(71) Applicant: Medtronic Ardian Luxembourg S.a.r.l., Luxembourg (LU)

(72) Inventors: Rudy Beasley, Rohnert Park, CA (US); Leonel Mendoza, Santa Rosa, CA (US); Martha A. Barajas-Torres, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 746 days.

(21) Appl. No.: 14/891,652

(22) PCT Filed: May 16, 2014

(86) PCT No.: PCT/US2014/038479
§ 371 (c)(1),
(2) Date: Nov. 16, 2015

(87) PCT Pub. No.: WO2014/189794
PCT Pub. Date: Nov. 27, 2014

(65) Prior Publication Data
US 2016/0135879 A1   May 19, 2016

Related U.S. Application Data

(60) Provisional application No. 61/825,026, filed on May 18, 2013, provisional application No. 61/887,927, filed on Oct. 7, 2013.

(51) Int. Cl.
*A61B 18/14* (2006.01)
*A61M 25/00* (2006.01)
(Continued)

(52) U.S. Cl.
CPC ..... *A61B 18/1492* (2013.01); *A61M 25/0054* (2013.01); *A61M 25/09* (2013.01);
(Continued)

(58) Field of Classification Search
CPC ........ A61B 18/1492; A61B 2018/1407; A61B 2018/1435; A61B 2018/144;
(Continued)

(56) References Cited

U.S. PATENT DOCUMENTS

| 4,020,829 A | 5/1977 | Wilson et al. |
| 4,602,624 A | 7/1986 | Naples et al. |

(Continued)

FOREIGN PATENT DOCUMENTS

| CN | 2782017 | 5/2006 |
| CN | 101084038 | 12/2007 |

(Continued)

OTHER PUBLICATIONS

U.S. Appl. No. 95/002,110, filed Aug. 29, 2012, Demarais et al.
(Continued)

*Primary Examiner* — Thomas A Giuliani
(74) *Attorney, Agent, or Firm* — Snell & Wilmer, LLP

(57) ABSTRACT

Neuromodulation catheters with shafts for enhanced flexibility and control and methods of making and using the catheters. A neuromodulation catheter can include an elongated shaft having a distal end portion and a mandrel extending at least along the distal end portion. The mandrel can have an at least substantially solid core. The neuromodulation catheter can further include a transition member and a neuromodulation assembly coupled to the transition member. The transition member can have a proximal portion, a distal portion, and a guide wire lumen extending through the proximal and distal portions. The neuromodulation assembly can extend distally from the distal portion of
(Continued)

the transition member, and the mandrel can extend proximally from the proximal portion of the transition member.

18 Claims, 10 Drawing Sheets

(51) Int. Cl.
  *A61M 25/09* (2006.01)
  *A61N 1/28* (2006.01)
  *A61B 18/00* (2006.01)
  *A61M 25/01* (2006.01)

(52) U.S. Cl.
  CPC ...... *A61N 1/28* (2013.01); *A61B 2018/00404* (2013.01); *A61B 2018/00434* (2013.01); *A61B 2018/00505* (2013.01); *A61B 2018/00577* (2013.01); *A61B 2018/1467* (2013.01); *A61M 2025/0183* (2013.01)

(58) Field of Classification Search
  CPC .... A61B 2018/1465; A61B 2018/1475; A61B 2018/1467; A61B 2018/00214; A61B 2018/0016; A61B 2018/00505; A61B 2018/00267; A61B 2018/00577; A61B 2018/00404; A61B 2018/00434; A61B 2018/00511; A61B 2018/0212; A61N 1/28; A61M 2025/0063; A61M 2025/0064
  USPC .............. 606/21–23, 27, 28, 41, 46, 47; 607/98–101, 113, 115, 116
  See application file for complete search history.

(56) References Cited

U.S. PATENT DOCUMENTS

| | | |
|---|---|---|
| 4,649,936 A | 3/1987 | Ungar et al. |
| 4,764,504 A | 8/1988 | Johnson et al. |
| 4,890,623 A | 1/1990 | Cook et al. |
| 4,976,711 A | 12/1990 | Parins et al. |
| 4,998,923 A | 3/1991 | Samson et al. |
| 5,158,564 A | 10/1992 | Schnepp-Pesch et al. |
| 5,300,068 A | 4/1994 | Rosar et al. |
| 5,322,064 A | 6/1994 | Lundquist |
| 5,322,505 A | 6/1994 | Krause et al. |
| 5,358,514 A | 10/1994 | Schulman et al. |
| 5,368,591 A | 11/1994 | Lennox et al. |
| 5,368,592 A | 11/1994 | Stern et al. |
| 5,399,164 A | 3/1995 | Snoke et al. |
| 5,423,744 A | 6/1995 | Gencheff et al. |
| 5,425,364 A | 6/1995 | Imran |
| 5,437,288 A | 8/1995 | Schwartz et al. |
| 5,441,483 A | 8/1995 | Avitall |
| 5,445,148 A | 8/1995 | Jaraczewski et al. |
| 5,454,788 A | 10/1995 | Walker et al. |
| 5,477,856 A | 12/1995 | Lundquist |
| 5,484,400 A | 1/1996 | Edwards et al. |
| 5,545,200 A | 8/1996 | West et al. |
| 5,554,114 A | 9/1996 | Wallace et al. |
| 5,558,643 A | 9/1996 | Samson et al. |
| 5,571,147 A | 11/1996 | Sluijter et al. |
| 5,582,609 A | 12/1996 | Swanson et al. |
| 5,588,964 A | 12/1996 | Imran et al. |
| 5,599,319 A | 2/1997 | Stevens |
| 5,599,345 A | 2/1997 | Edwards et al. |
| 5,626,576 A | 5/1997 | Janssen |
| 5,628,775 A | 5/1997 | Jackson et al. |
| 5,672,174 A | 9/1997 | Gough et al. |
| 5,685,868 A | 11/1997 | Lundquist |
| 5,688,266 A | 11/1997 | Edwards et al. |
| 5,690,666 A | 11/1997 | Berenstein et al. |
| 5,695,506 A | 12/1997 | Pike et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,741,429 A | 4/1998 | Donadio, III et al. |
| 5,743,903 A | 4/1998 | Stern et al. |
| 5,772,590 A | 6/1998 | Webster, Jr. |
| 5,807,249 A | 9/1998 | Qin et al. |
| 5,823,955 A | 10/1998 | Kuck et al. |
| 5,827,272 A | 10/1998 | Breining et al. |
| 5,865,787 A | 2/1999 | Shapland et al. |
| 5,871,444 A | 2/1999 | Ouchi |
| 5,891,110 A | 4/1999 | Larson et al. |
| 5,891,114 A | 4/1999 | Chien et al. |
| 5,893,885 A | 4/1999 | Webster et al. |
| 5,895,378 A | 4/1999 | Nita |
| 5,904,667 A | 5/1999 | Falwell |
| 5,916,178 A | 6/1999 | Noone et al. |
| 5,916,214 A | 6/1999 | Cosio et al. |
| 5,931,830 A | 8/1999 | Jacobsen et al. |
| 5,935,102 A | 8/1999 | Bowden et al. |
| 5,935,124 A | 8/1999 | Klumb et al. |
| 5,944,710 A | 8/1999 | Dev et al. |
| 5,951,539 A | 9/1999 | Nita et al. |
| 5,954,719 A | 9/1999 | Chen et al. |
| 5,961,511 A | 10/1999 | Mortier et al. |
| 5,967,978 A | 10/1999 | Littmann et al. |
| 5,971,975 A | 10/1999 | Mills et al. |
| 5,980,563 A | 11/1999 | Tu et al. |
| 5,983,141 A | 11/1999 | Sluijter et al. |
| 5,987,344 A | 11/1999 | West |
| 6,004,269 A | 12/1999 | Crowley et al. |
| 6,009,877 A | 1/2000 | Edwards |
| 6,024,730 A | 2/2000 | Pagan |
| 6,024,740 A | 2/2000 | Lesh et al. |
| 6,036,687 A | 3/2000 | Laufer et al. |
| 6,048,338 A | 4/2000 | Larson et al. |
| 6,053,922 A | 4/2000 | Krause et al. |
| 6,059,769 A | 5/2000 | Lunn et al. |
| 6,066,134 A | 5/2000 | Eggers et al. |
| 6,079,414 A | 6/2000 | Roth |
| 6,080,171 A | 6/2000 | Keith et al. |
| 6,090,104 A | 7/2000 | Webster, Jr. |
| 6,091,995 A | 7/2000 | Ingle et al. |
| 6,099,524 A | 8/2000 | Lipson et al. |
| 6,102,890 A | 8/2000 | Stivland et al. |
| 6,110,187 A | 8/2000 | Donlon |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,159,187 A | 12/2000 | Park et al. |
| 6,161,048 A | 12/2000 | Sluijter et al. |
| 6,165,163 A | 12/2000 | Chien et al. |
| 6,179,857 B1 | 1/2001 | Diaz et al. |
| 6,210,362 B1 | 4/2001 | Ponzi |
| 6,210,406 B1 | 4/2001 | Webster |
| 6,213,974 B1 | 4/2001 | Smith et al. |
| 6,219,577 B1 | 4/2001 | Brown, III et al. |
| 6,224,592 B1 | 5/2001 | Eggers et al. |
| 6,245,020 B1 | 6/2001 | Moore et al. |
| 6,245,045 B1 | 6/2001 | Stratienko |
| 6,246,912 B1 | 6/2001 | Sluijter et al. |
| 6,246,914 B1 | 6/2001 | de la Rama et al. |
| 6,251,092 B1 | 6/2001 | Qin et al. |
| 6,254,588 B1 | 7/2001 | Jones et al. |
| 6,263,224 B1 | 7/2001 | West |
| 6,273,876 B1 | 8/2001 | Klima et al. |
| 6,273,886 B1 | 8/2001 | Edwards et al. |
| 6,283,951 B1 | 9/2001 | Flaherty et al. |
| 6,283,960 B1 | 9/2001 | Ashley |
| 6,287,301 B1 | 9/2001 | Thompson et al. |
| 6,287,318 B1 | 9/2001 | Villar et al. |
| 6,292,695 B1 | 9/2001 | Webster, Jr. et al. |
| 6,293,943 B1 | 9/2001 | Panescu et al. |
| 6,298,256 B1 | 10/2001 | Meyer |
| 6,299,623 B1 | 10/2001 | Wulfman |
| 6,314,325 B1 | 11/2001 | Fitz |
| 6,322,558 B1 | 11/2001 | Taylor et al. |
| 6,322,559 B1 | 11/2001 | Daulton et al. |
| 6,346,074 B1 | 2/2002 | Roth |

(56) References Cited

U.S. PATENT DOCUMENTS

| | | |
|---|---|---|
| 6,371,965 B2 | 4/2002 | Gifford, III et al. |
| 6,387,075 B1 | 5/2002 | Stivland et al. |
| 6,387,105 B1 | 5/2002 | Gifford, III et al. |
| 6,401,720 B1 | 6/2002 | Stevens et al. |
| 6,405,732 B1 | 6/2002 | Edwards et al. |
| 6,413,255 B1 | 7/2002 | Stern |
| 6,427,089 B1 | 7/2002 | Knowlton |
| 6,443,965 B1 | 9/2002 | Gifford, III et al. |
| 6,451,034 B1 | 9/2002 | Gifford, III et al. |
| 6,454,775 B1 | 9/2002 | Demarais et al. |
| 6,475,209 B1 | 11/2002 | Larson et al. |
| 6,482,202 B1 | 11/2002 | Goble et al. |
| 6,488,679 B1 | 12/2002 | Swanson et al. |
| 6,491,705 B2 | 12/2002 | Gifford, III et al. |
| 6,497,711 B1 | 12/2002 | Plaia et al. |
| 6,500,172 B1 | 12/2002 | Panescu et al. |
| 6,506,189 B1 | 1/2003 | Rittman, III et al. |
| 6,508,804 B2 | 1/2003 | Sarge et al. |
| 6,514,226 B1 | 2/2003 | Levin et al. |
| 6,514,236 B1 | 2/2003 | Stratienko |
| 6,517,572 B2 | 2/2003 | Kugler et al. |
| 6,522,926 B1 | 2/2003 | Kieval et al. |
| 6,542,781 B1 * | 4/2003 | Koblish ............. A61B 18/1492 607/122 |
| 6,549,800 B1 | 4/2003 | Atalar et al. |
| 6,562,034 B2 | 5/2003 | Edwards et al. |
| 6,565,582 B2 | 5/2003 | Gifford, III et al. |
| 6,569,177 B1 | 5/2003 | Dillard et al. |
| 6,585,718 B2 | 7/2003 | Hayzelden et al. |
| 6,610,046 B1 | 8/2003 | Usami et al. |
| 6,611,720 B2 | 8/2003 | Hata et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,628,976 B1 | 9/2003 | Fuimaono et al. |
| 6,632,193 B1 | 10/2003 | Davison et al. |
| 6,635,054 B2 | 10/2003 | Fjield et al. |
| 6,640,120 B1 | 10/2003 | Swanson et al. |
| 6,648,854 B1 | 11/2003 | Patterson et al. |
| 6,651,672 B2 | 11/2003 | Roth |
| 6,656,195 B2 | 12/2003 | Peters et al. |
| 6,659,981 B2 | 12/2003 | Stewart et al. |
| 6,669,670 B1 | 12/2003 | Muni et al. |
| 6,669,692 B1 | 12/2003 | Nelson et al. |
| 6,676,678 B2 | 1/2004 | Gifford, III et al. |
| 6,679,268 B2 | 1/2004 | Stevens et al. |
| 6,682,541 B1 | 1/2004 | Gifford, III et al. |
| 6,685,648 B2 | 2/2004 | Flaherty et al. |
| 6,695,857 B2 | 2/2004 | Gifford, III et al. |
| 6,699,257 B2 | 3/2004 | Gifford, III et al. |
| 6,702,811 B2 | 3/2004 | Stewart et al. |
| 6,706,010 B1 | 3/2004 | Miki et al. |
| 6,711,444 B2 | 3/2004 | Koblish |
| 6,716,207 B2 | 4/2004 | Farnholtz |
| 6,723,043 B2 | 4/2004 | Kleeman et al. |
| 6,736,835 B2 | 5/2004 | Pellegrino et al. |
| 6,745,080 B2 | 6/2004 | Koblish |
| 6,749,560 B1 | 6/2004 | Konstorum et al. |
| 6,752,805 B2 | 6/2004 | Maguire et al. |
| 6,770,070 B1 | 8/2004 | Balbierz |
| 6,790,206 B2 | 9/2004 | Panescu |
| 6,817,999 B2 | 11/2004 | Berube et al. |
| 6,829,497 B2 | 12/2004 | Mogul |
| 6,830,568 B1 | 12/2004 | Kesten et al. |
| 6,845,267 B2 | 1/2005 | Harrison et al. |
| 6,849,075 B2 | 2/2005 | Bertolero et al. |
| 6,850,801 B2 | 2/2005 | Kieval et al. |
| 6,884,260 B2 | 4/2005 | Kugler et al. |
| 6,885,888 B2 | 4/2005 | Rezai |
| 6,889,694 B2 | 5/2005 | Hooven |
| 6,890,329 B2 | 5/2005 | Carroll et al. |
| 6,893,436 B2 | 5/2005 | Woodard et al. |
| 6,909,009 B2 | 6/2005 | Koridze |
| 6,915,806 B2 | 7/2005 | Pacek et al. |
| 6,926,669 B1 | 8/2005 | Stewart et al. |
| 6,926,713 B2 | 8/2005 | Rioux et al. |
| 6,939,346 B2 | 9/2005 | Kannenberg et al. |
| 6,945,956 B2 | 9/2005 | Waldhauser et al. |
| 6,949,097 B2 | 9/2005 | Stewart et al. |
| 6,955,175 B2 | 10/2005 | Stevens et al. |
| 6,966,908 B2 | 11/2005 | Maguire et al. |
| 6,984,238 B2 | 1/2006 | Gifford, III et al. |
| 7,058,456 B2 | 6/2006 | Pierce |
| 7,087,051 B2 | 8/2006 | Bourne et al. |
| 7,100,614 B2 | 9/2006 | Stevens et al. |
| 7,102,151 B2 | 9/2006 | Reinberg et al. |
| 7,110,828 B2 | 9/2006 | Kolberg et al. |
| 7,112,211 B2 | 9/2006 | Gifford, III et al. |
| 7,115,183 B2 | 10/2006 | Larson et al. |
| 7,119,183 B2 | 10/2006 | Seed et al. |
| 7,128,718 B2 | 10/2006 | Hojeibane et al. |
| 7,137,990 B2 | 11/2006 | Hebert et al. |
| 7,149,574 B2 | 12/2006 | Yun et al. |
| 7,153,315 B2 | 12/2006 | Miller |
| 7,162,303 B2 | 1/2007 | Levin et al. |
| 7,171,275 B2 | 1/2007 | Hata et al. |
| 7,172,610 B2 | 2/2007 | Heitzmann et al. |
| 7,184,811 B2 | 2/2007 | Phan et al. |
| 7,192,427 B2 | 3/2007 | Chapelon et al. |
| 7,221,979 B2 | 5/2007 | Zhou et al. |
| 7,238,184 B2 | 7/2007 | Megerman et al. |
| 7,241,273 B2 | 7/2007 | Maguire et al. |
| 7,276,062 B2 | 10/2007 | McDaniel et al. |
| 7,294,127 B2 | 11/2007 | Leung et al. |
| 7,311,705 B2 | 12/2007 | Sra |
| 7,338,467 B2 | 3/2008 | Lutter |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,393,338 B2 | 7/2008 | Nita |
| 7,402,151 B2 | 7/2008 | Rosenman et al. |
| 7,486,805 B2 | 2/2009 | Krattiger |
| 7,488,338 B2 | 2/2009 | Eidenschink |
| 7,494,486 B2 | 2/2009 | Mische et al. |
| 7,494,488 B2 | 2/2009 | Weber |
| 7,497,858 B2 | 3/2009 | Chapelon et al. |
| 7,517,349 B2 | 4/2009 | Truckai et al. |
| 7,520,863 B2 | 4/2009 | Grewe et al. |
| 7,540,865 B2 | 6/2009 | Griffin et al. |
| 7,563,247 B2 | 7/2009 | Maguire et al. |
| 7,615,067 B2 | 11/2009 | Lee et al. |
| 7,617,005 B2 | 11/2009 | Demarais et al. |
| 7,620,451 B2 | 11/2009 | Demarais et al. |
| 7,637,903 B2 | 12/2009 | Lentz et al. |
| 7,647,115 B2 | 1/2010 | Levin et al. |
| 7,653,438 B2 | 1/2010 | Deem et al. |
| 7,682,319 B2 | 3/2010 | Martin et al. |
| 7,699,809 B2 | 4/2010 | Urmey |
| 7,702,397 B2 | 4/2010 | Fredricks et al. |
| 7,706,894 B2 | 4/2010 | Stewart et al. |
| 7,708,704 B2 | 5/2010 | Mitelberg et al. |
| 7,717,853 B2 | 5/2010 | Nita |
| 7,717,948 B2 | 5/2010 | Demarais et al. |
| 7,727,187 B2 | 6/2010 | Lentz |
| 7,744,586 B2 | 6/2010 | Larson et al. |
| 7,744,856 B2 | 6/2010 | DeFilippi et al. |
| 7,758,520 B2 | 7/2010 | Griffin et al. |
| 7,763,012 B2 | 7/2010 | Petrick et al. |
| 7,771,410 B2 | 8/2010 | Venturelli |
| 7,771,421 B2 | 8/2010 | Stewart et al. |
| 7,778,703 B2 | 8/2010 | Gross et al. |
| 7,780,646 B2 | 8/2010 | Farnholtz |
| 7,780,660 B2 | 8/2010 | Bourne et al. |
| 7,785,289 B2 | 8/2010 | Rios et al. |
| 7,806,871 B2 | 10/2010 | Li et al. |
| 7,811,265 B2 | 10/2010 | Hering et al. |
| 7,811,281 B1 | 10/2010 | Rentrop |
| 7,815,600 B2 | 10/2010 | Al-Marashi et al. |
| 7,815,637 B2 | 10/2010 | Ormsby et al. |
| 7,819,866 B2 | 10/2010 | Bednarek |
| 7,833,191 B2 | 11/2010 | Flach et al. |
| 7,846,157 B2 | 12/2010 | Kozel |
| 7,850,685 B2 | 12/2010 | Kunis et al. |
| 7,862,565 B2 | 1/2011 | Eder et al. |

(56) References Cited

U.S. PATENT DOCUMENTS

| | | |
|---|---|---|
| 7,863,897 B2 | 1/2011 | Slocum, Jr. et al. |
| 7,896,873 B2 | 3/2011 | Hiller et al. |
| 7,905,862 B2 | 3/2011 | Sampson |
| 7,914,467 B2 | 3/2011 | Layman et al. |
| 7,938,830 B2 | 5/2011 | Saadat et al. |
| 7,947,016 B2 | 5/2011 | Lentz |
| 7,967,816 B2 | 6/2011 | Ocel et al. |
| 7,989,042 B2 | 8/2011 | Obara et al. |
| 8,007,440 B2 | 8/2011 | Magnin et al. |
| 8,007,462 B2 | 8/2011 | Gibson et al. |
| 8,027,718 B2 | 9/2011 | Spinner et al. |
| 8,043,279 B2 | 10/2011 | Hisamatsu et al. |
| 8,043,288 B2 | 10/2011 | Dando et al. |
| 8,075,580 B2 | 12/2011 | Makower |
| 8,088,127 B2 | 1/2012 | Mayse et al. |
| 8,092,444 B2 | 1/2012 | Lentz et al. |
| 8,124,876 B2 | 2/2012 | Dayton et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,829 B2 | 5/2012 | Farnholtz |
| 8,175,711 B2 | 5/2012 | Demarais et al. |
| 8,190,238 B2 | 5/2012 | Moll et al. |
| 8,241,217 B2 | 8/2012 | Chiang et al. |
| 8,251,977 B2 | 8/2012 | Partlett |
| 8,292,881 B2 | 10/2012 | Brannan et al. |
| 8,343,145 B2 | 1/2013 | Brannan |
| 8,376,865 B2 | 2/2013 | Forster et al. |
| 8,388,680 B2 | 3/2013 | Starksen et al. |
| 8,398,629 B2 | 3/2013 | Thistle |
| 8,401,650 B2 | 3/2013 | Simon et al. |
| 8,409,193 B2 | 4/2013 | Young et al. |
| 8,409,195 B2 | 4/2013 | Young |
| 8,418,362 B2 | 4/2013 | Zerfas et al. |
| 8,473,023 B2 | 6/2013 | Worley et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,663,196 B2 | 3/2014 | Kassab et al. |
| 8,740,849 B1 | 6/2014 | Fischell et al. |
| 8,882,796 B2 | 11/2014 | Martinez |
| 8,974,451 B2 | 3/2015 | Smith |
| 9,044,575 B2 | 6/2015 | Beasley et al. |
| 9,162,046 B2 | 10/2015 | Hill et al. |
| 9,399,115 B2 | 7/2016 | Beasley et al. |
| 9,492,635 B2 | 11/2016 | Beasley et al. |
| 9,844,643 B2 | 12/2017 | Beasley et al. |
| 2002/0020417 A1 | 2/2002 | Nikolchev et al. |
| 2002/0022864 A1 | 2/2002 | Mahvi et al. |
| 2002/0062123 A1 | 5/2002 | McClurken et al. |
| 2002/0082584 A1 | 6/2002 | Rosenman et al. |
| 2002/0087208 A1 | 7/2002 | Koblish et al. |
| 2002/0107515 A1 | 8/2002 | Edwards et al. |
| 2002/0165532 A1 | 11/2002 | Hill et al. |
| 2002/0183682 A1 | 12/2002 | Darvish et al. |
| 2003/0004510 A1 | 1/2003 | Wham et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0065317 A1 | 4/2003 | Rudie et al. |
| 2003/0074039 A1 | 4/2003 | Puskas |
| 2003/0092995 A1 | 5/2003 | Thompson |
| 2003/0093059 A1 | 5/2003 | Griffin et al. |
| 2003/0125790 A1 | 7/2003 | Fastovsky et al. |
| 2003/0139689 A1 | 7/2003 | Shturman et al. |
| 2003/0181897 A1 | 9/2003 | Thomas et al. |
| 2003/0191451 A1 | 10/2003 | Gilmartin |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0220639 A1 | 11/2003 | Chapelon et al. |
| 2003/0229340 A1 | 12/2003 | Sherry et al. |
| 2004/0006359 A1 | 1/2004 | Laguna |
| 2004/0010289 A1 | 1/2004 | Biggs et al. |
| 2004/0073206 A1 | 4/2004 | Foley et al. |
| 2004/0088002 A1 | 5/2004 | Boyle et al. |
| 2004/0098028 A1 | 5/2004 | Martinez |
| 2004/0167509 A1 | 8/2004 | Taimisto |
| 2004/0215186 A1 | 10/2004 | Cornelius et al. |
| 2005/0004515 A1 | 1/2005 | Hart et al. |
| 2005/0010095 A1 | 1/2005 | Stewart et al. |
| 2005/0080400 A1 | 4/2005 | Corcoran et al. |
| 2005/0080409 A1 | 4/2005 | Young et al. |
| 2005/0096647 A1 | 5/2005 | Steinke et al. |
| 2005/0171572 A1 | 8/2005 | Martinez |
| 2005/0187579 A1 | 8/2005 | Danek et al. |
| 2005/0228286 A1 | 10/2005 | Messerly et al. |
| 2005/0228460 A1 | 10/2005 | Levin et al. |
| 2005/0251094 A1 | 11/2005 | Peterson |
| 2005/0253680 A1 | 11/2005 | Mathews et al. |
| 2005/0273006 A1 | 12/2005 | Stewart et al. |
| 2006/0004323 A1 | 1/2006 | Chang |
| 2006/0004346 A1 | 1/2006 | Begg |
| 2006/0020327 A1 | 1/2006 | Lashinski et al. |
| 2006/0025765 A1 | 2/2006 | Landman et al. |
| 2006/0064055 A1 | 3/2006 | Pile-Spellman et al. |
| 2006/0064123 A1 | 3/2006 | Bonnette et al. |
| 2006/0074403 A1 | 4/2006 | Rafiee |
| 2006/0079926 A1 | 4/2006 | Desai et al. |
| 2006/0085054 A1 | 4/2006 | Zikorus et al. |
| 2006/0089637 A1 | 4/2006 | Werneth et al. |
| 2006/0095029 A1 | 5/2006 | Young et al. |
| 2006/0100618 A1 | 5/2006 | Chan et al. |
| 2006/0100687 A1 | 5/2006 | Fahey et al. |
| 2006/0122587 A1 | 6/2006 | Sharareh |
| 2006/0142753 A1 | 6/2006 | Francischelli et al. |
| 2006/0167498 A1 | 7/2006 | DiLorenzo |
| 2006/0184221 A1 | 8/2006 | Stewart et al. |
| 2006/0206150 A1 | 9/2006 | Demarais et al. |
| 2006/0212076 A1 | 9/2006 | Demarais et al. |
| 2006/0224112 A1 | 10/2006 | Lentz |
| 2006/0224153 A1 | 10/2006 | Fischell et al. |
| 2006/0263393 A1 | 11/2006 | Demopulos et al. |
| 2006/0271111 A1 | 11/2006 | Demarais et al. |
| 2006/0276846 A1 | 12/2006 | Malecki et al. |
| 2006/0287644 A1 | 12/2006 | Inganas et al. |
| 2007/0005009 A1 | 1/2007 | Larson et al. |
| 2007/0027390 A1 | 2/2007 | Maschke et al. |
| 2007/0049924 A1 | 3/2007 | Rahn |
| 2007/0049999 A1 | 3/2007 | Esch et al. |
| 2007/0067008 A1 | 3/2007 | Scheiner et al. |
| 2007/0073151 A1 | 3/2007 | Lee |
| 2007/0073331 A1 | 3/2007 | Brown et al. |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0129720 A1 | 6/2007 | Demarais et al. |
| 2007/0149963 A1 | 6/2007 | Matsukuma et al. |
| 2007/0156114 A1 | 7/2007 | Worley et al. |
| 2007/0179496 A1 | 8/2007 | Swoyer et al. |
| 2007/0197891 A1 | 8/2007 | Shachar et al. |
| 2007/0213687 A1 | 9/2007 | Barlow |
| 2007/0233039 A1 | 10/2007 | Mitelberg |
| 2007/0265687 A1 | 11/2007 | Deem et al. |
| 2007/0270779 A1 | 11/2007 | Jacobs et al. |
| 2007/0287955 A1 | 12/2007 | Layman et al. |
| 2008/0004658 A1 | 1/2008 | Malecki et al. |
| 2008/0015562 A1 | 1/2008 | Hong et al. |
| 2008/0071269 A1 | 3/2008 | Hilario et al. |
| 2008/0077119 A1 | 3/2008 | Snyder et al. |
| 2008/0086047 A1 | 4/2008 | McDaniel et al. |
| 2008/0091193 A1 | 4/2008 | Kauphusman et al. |
| 2008/0097397 A1 | 4/2008 | Vrba |
| 2008/0108867 A1 | 5/2008 | Zhou |
| 2008/0140072 A1 | 6/2008 | Stangenes et al. |
| 2008/0147001 A1 | 6/2008 | Al-Marashi et al. |
| 2008/0172037 A1 | 7/2008 | Huang et al. |
| 2008/0177205 A1 | 7/2008 | Rama et al. |
| 2008/0221620 A1 | 9/2008 | Krause |
| 2008/0287918 A1 | 11/2008 | Rosenman et al. |

(56) References Cited

U.S. PATENT DOCUMENTS

| | | |
|---|---|---|
| 2008/0319418 A1 | 12/2008 | Chong |
| 2008/0319513 A1 | 12/2008 | Pu et al. |
| 2009/0012465 A1 | 1/2009 | Latini |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0062772 A1* | 3/2009 | Wakeford ......... A61M 25/0127 604/516 |
| 2009/0069671 A1 | 3/2009 | Anderson |
| 2009/0118620 A1 | 5/2009 | Tgavalekos et al. |
| 2009/0125001 A1 | 5/2009 | Anderson et al. |
| 2009/0149848 A1 | 6/2009 | Werneth et al. |
| 2009/0157048 A1 | 6/2009 | Sutermeister et al. |
| 2009/0163850 A1 | 6/2009 | Betts et al. |
| 2009/0171333 A1 | 7/2009 | Hon |
| 2009/0221955 A1 | 9/2009 | Babaev |
| 2009/0306650 A1 | 12/2009 | Govari et al. |
| 2009/0312606 A1 | 12/2009 | Dayton et al. |
| 2010/0010526 A1 | 1/2010 | Mitusina |
| 2010/0010533 A1 | 1/2010 | Burke et al. |
| 2010/0030061 A1 | 2/2010 | Canfield et al. |
| 2010/0030217 A1 | 2/2010 | Mitusina |
| 2010/0057037 A1 | 3/2010 | Webler |
| 2010/0069882 A1 | 3/2010 | Jennings et al. |
| 2010/0099952 A1 | 4/2010 | Adams |
| 2010/0100073 A1 | 4/2010 | Lentz et al. |
| 2010/0137860 A1 | 6/2010 | Demarais et al. |
| 2010/0137952 A1 | 6/2010 | Demarais et al. |
| 2010/0168740 A1 | 7/2010 | Stewart et al. |
| 2010/0179512 A1 | 7/2010 | Chong et al. |
| 2010/0191112 A1 | 7/2010 | Demarais et al. |
| 2010/0217184 A1 | 8/2010 | Koblish et al. |
| 2010/0222851 A1 | 9/2010 | Deem et al. |
| 2010/0222854 A1 | 9/2010 | Demarais et al. |
| 2010/0228112 A1 | 9/2010 | Von Malmborg |
| 2010/0249604 A1 | 9/2010 | Hastings et al. |
| 2010/0305682 A1 | 12/2010 | Furst |
| 2010/0312141 A1 | 12/2010 | Keast et al. |
| 2010/0324482 A1 | 12/2010 | Farnholtz |
| 2010/0331618 A1 | 12/2010 | Galperin |
| 2010/0331776 A1 | 12/2010 | Salahieh et al. |
| 2011/0015675 A1 | 1/2011 | Howard et al. |
| 2011/0021976 A1 | 1/2011 | Li et al. |
| 2011/0028962 A1 | 2/2011 | Werneth et al. |
| 2011/0034989 A1 | 2/2011 | Al-Marashi et al. |
| 2011/0054464 A1 | 3/2011 | Werneth et al. |
| 2011/0054465 A1 | 3/2011 | Werneth et al. |
| 2011/0066105 A1 | 3/2011 | Hart et al. |
| 2011/0071400 A1 | 3/2011 | Hastings et al. |
| 2011/0071401 A1 | 3/2011 | Hastings et al. |
| 2011/0087066 A1 | 4/2011 | Boutillette et al. |
| 2011/0112476 A1 | 5/2011 | Kauphusman et al. |
| 2011/0208194 A1 | 8/2011 | Steiner et al. |
| 2011/0245808 A1 | 10/2011 | Voeller et al. |
| 2011/0270173 A1 | 11/2011 | Gibson et al. |
| 2011/0276034 A1 | 11/2011 | Tomarelli et al. |
| 2011/0288392 A1 | 11/2011 | de la Rama et al. |
| 2012/0059241 A1 | 3/2012 | Hastings et al. |
| 2012/0089047 A1 | 4/2012 | Ryba et al. |
| 2012/0101413 A1 | 4/2012 | Beetel et al. |
| 2012/0116382 A1* | 5/2012 | Ku .................... A61B 18/1492 606/33 |
| 2012/0123328 A1 | 5/2012 | Williams |
| 2012/0130289 A1 | 5/2012 | Demarais et al. |
| 2012/0130345 A1 | 5/2012 | Levin et al. |
| 2012/0143293 A1 | 6/2012 | Mauch et al. |
| 2012/0172837 A1 | 7/2012 | Demarais et al. |
| 2012/0197246 A1 | 8/2012 | Mauch |
| 2012/0204387 A1 | 8/2012 | Carlson et al. |
| 2012/0232529 A1 | 9/2012 | Buckley et al. |
| 2012/0265066 A1 | 10/2012 | Crow et al. |
| 2013/0006238 A1 | 1/2013 | Ditter et al. |
| 2013/0006291 A1 | 1/2013 | Harari et al. |
| 2013/0035681 A1 | 2/2013 | Subramaniam et al. |
| 2013/0090647 A1 | 4/2013 | Smith |
| 2013/0090649 A1 | 4/2013 | Smith et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0116685 A1 | 5/2013 | Deem et al. |
| 2013/0116693 A1 | 5/2013 | Nelson et al. |
| 2013/0123770 A1 | 5/2013 | Smith |
| 2013/0131667 A1 | 5/2013 | Jenson et al. |
| 2013/0131743 A1 | 5/2013 | Yamasaki et al. |
| 2013/0172879 A1 | 7/2013 | Sutermeister et al. |
| 2013/0172881 A1 | 7/2013 | Hill et al. |
| 2013/0184642 A1 | 7/2013 | O'Donnell et al. |
| 2013/0184703 A1 | 7/2013 | Shireman et al. |
| 2013/0190801 A1 | 7/2013 | Divino et al. |
| 2013/0274730 A1 | 10/2013 | Anderson et al. |
| 2013/0274731 A1 | 10/2013 | Anderson et al. |
| 2013/0274737 A1 | 10/2013 | Wang et al. |
| 2013/0304062 A1* | 11/2013 | Chan .................. A61B 18/1492 606/41 |
| 2014/0094787 A1 | 4/2014 | Reynolds |
| 2014/0114288 A1 | 4/2014 | Beasley et al. |
| 2014/0121641 A1 | 5/2014 | Fischell et al. |
| 2014/0121644 A1 | 5/2014 | Fischell et al. |
| 2014/0135755 A1 | 5/2014 | Sutermeister et al. |
| 2014/0136350 A1 | 5/2014 | Savolainen |
| 2014/0214026 A1 | 7/2014 | Degen |
| 2014/0249524 A1 | 9/2014 | Kocur |
| 2014/0276613 A1 | 9/2014 | Goodman et al. |
| 2014/0276752 A1 | 9/2014 | Wang et al. |
| 2014/0276787 A1 | 9/2014 | Wang et al. |
| 2014/0358079 A1 | 12/2014 | Fischell et al. |
| 2014/0378967 A1 | 12/2014 | Willard et al. |
| 2015/0231367 A1 | 8/2015 | Salstrom et al. |
| 2015/0265339 A1 | 9/2015 | Lindquist et al. |
| 2017/0021168 A1 | 1/2017 | Yun et al. |

FOREIGN PATENT DOCUMENTS

| | | |
|---|---|---|
| CN | 102125460 | 7/2011 |
| CN | 102125725 | 7/2011 |
| CN | 102885648 | 1/2013 |
| CN | 102908188 | 2/2013 |
| DE | 102005041601 | 4/2007 |
| DE | 102012104705 | 12/2013 |
| EP | 0348136 | 12/1989 |
| EP | 0352955 | 1/1990 |
| EP | 0512359 | 11/1992 |
| EP | 0521595 | 1/1993 |
| EP | 0542246 | 5/1993 |
| EP | 626818 | 12/1994 |
| EP | 647435 | 4/1995 |
| EP | 652026 | 5/1995 |
| EP | 664990 | 8/1995 |
| EP | 0680351 | 11/1995 |
| EP | 0680355 | 11/1995 |
| EP | 727184 | 8/1996 |
| EP | 0787019 | 8/1997 |
| EP | 0834289 | 4/1998 |
| EP | 862478 | 9/1998 |
| EP | 0937481 | 8/1999 |
| EP | 944353 | 9/1999 |
| EP | 0951244 | 10/1999 |
| EP | 0984806 | 3/2000 |
| EP | 1286625 | 3/2003 |
| EP | 1326550 | 7/2003 |
| EP | 1334743 | 8/2003 |
| EP | 1374943 | 1/2004 |
| EP | 1656963 | 5/2006 |
| EP | 1709922 | 10/2006 |
| EP | 1768732 | 4/2007 |
| EP | 1787674 | 5/2007 |
| EP | 1824548 | 8/2007 |
| EP | 1827558 | 9/2007 |
| EP | 1839697 | 10/2007 |
| EP | 1857134 | 11/2007 |
| EP | 1906853 | 4/2008 |
| EP | 1968679 | 9/2008 |

(56) References Cited

FOREIGN PATENT DOCUMENTS

| | | |
|---|---|---|
| EP | 1982741 | 10/2008 |
| EP | 2027882 | 2/2009 |
| EP | 2106821 | 10/2009 |
| EP | 2320821 | 5/2011 |
| EP | 2332607 | 6/2011 |
| EP | 2340765 | 7/2011 |
| EP | 2351593 | 8/2011 |
| EP | 2389974 | 11/2011 |
| EP | 2398540 | 12/2011 |
| EP | 2445568 | 5/2012 |
| EP | 2747688 | 7/2014 |
| EP | 2759314 | 7/2014 |
| EP | 2804554 | 11/2014 |
| EP | 2900160 | 8/2015 |
| EP | 2900161 | 8/2015 |
| EP | 2990070 | 3/2016 |
| EP | 3010436 | 4/2016 |
| EP | 2768563 | 11/2016 |
| WO | WO-9101772 | 2/1991 |
| WO | WO-9215356 | 9/1992 |
| WO | WO-199407446 | 4/1994 |
| WO | WO-9419039 | 9/1994 |
| WO | WO-9428809 | 12/1994 |
| WO | WO-1995025472 | 9/1995 |
| WO | WO-9531142 | 11/1995 |
| WO | WO-9703611 | 2/1997 |
| WO | WO-9729800 | 8/1997 |
| WO | WO-1997036548 | 10/1997 |
| WO | WO-9748435 | 12/1997 |
| WO | 1998042403 | 10/1998 |
| WO | WO-9843530 | 10/1998 |
| WO | WO-9848885 | 11/1998 |
| WO | WO-9850098 | 11/1998 |
| WO | WO-9852637 | 11/1998 |
| WO | WO-9900060 | 1/1999 |
| WO | WO-9911313 | 3/1999 |
| WO | WO-2001022897 | 4/2001 |
| WO | WO-0137746 | 5/2001 |
| WO | WO-200137723 | 5/2001 |
| WO | WO-2001070114 | 9/2001 |
| WO | WO-0230310 | 4/2002 |
| WO | WO-02080766 | 10/2002 |
| WO | WO-02089908 | 11/2002 |
| WO | WO-2003022167 | 3/2003 |
| WO | WO-2003/082080 | 10/2003 |
| WO | WO-2005030072 | 4/2005 |
| WO | WO-2005041748 | 5/2005 |
| WO | WO-2005/110528 | 11/2005 |
| WO | WO-2006/009588 | 1/2006 |
| WO | WO-2006041881 | 4/2006 |
| WO | WO-2006065949 | 6/2006 |
| WO | WO-2006105121 | 10/2006 |
| WO | WO-2007008954 | 1/2007 |
| WO | WO-2007059277 | 5/2007 |
| WO | WO-2007078997 | 7/2007 |
| WO | WO-2007117359 | 10/2007 |
| WO | WO-2008010150 | 1/2008 |
| WO | WO-2008036281 | 3/2008 |
| WO | WO-2008049084 | 4/2008 |
| WO | WO-2008064399 | 6/2008 |
| WO | WO-2008101244 | 8/2008 |
| WO | WO-2008139347 | 11/2008 |
| WO | WO-2009082635 | 7/2009 |
| WO | WO-2009088678 | 7/2009 |
| WO | WO-2009108997 | 9/2009 |
| WO | WO-2009125575 | 10/2009 |
| WO | WO-2009137819 | 11/2009 |
| WO | WO-2010091701 | 8/2010 |
| WO | WO-2010134503 | 11/2010 |
| WO | WO-2011056311 | 5/2011 |
| WO | WO-2011137377 | 11/2011 |
| WO | WO-2012100095 | 7/2012 |
| WO | WO-2013016203 | 1/2013 |
| WO | WO-2013/055685 | 4/2013 |
| WO | WO-2013055537 | 4/2013 |
| WO | WO-2013055815 | 4/2013 |
| WO | WO-2013055826 | 4/2013 |
| WO | WO-2013056672 | 4/2013 |
| WO | WO-2013058962 | 4/2013 |
| WO | WO-2013106054 | 7/2013 |
| WO | WO-2013109318 | 7/2013 |
| WO | WO-2013158676 | 10/2013 |
| WO | WO-2013158678 | 10/2013 |
| WO | WO-2014012282 | 1/2014 |
| WO | WO-2014036163 | 3/2014 |
| WO | WO-2014066432 | 5/2014 |
| WO | WO-2014066439 | 5/2014 |
| WO | 2014174662 | 10/2014 |
| WO | WO-2014/189794 | 11/2014 |
| WO | 2016090175 | 6/2016 |

OTHER PUBLICATIONS

U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

(56) References Cited

OTHER PUBLICATIONS

"The Edison Awards™" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty For The Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global SYMPLICITY registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action, U.S. Appl. No. 12/827,700, dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.

Gelfand, M., et al., "Treatment of renal failure and hypertension." U.S. Appl. No. 60/442,970, Jan. 29, 2003, 23 pages.

Gertner, Jon, "Meet The Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." Am. J. Roentgenol, 174: 1592-1594 (2000).

Han, Y.-M, et al., "Renal artery ebolization with diluted hot contrast medium: An experimental study." J Vasc Interv Radiol, 12: 862-868 (2001).

Hansen, J. M., et al. "The transplanted human kidney does not achieve functional reinnervation." Clin. Sci, 87: 13-19 (1994).

Hendee, W. R. et al. "Use of Animals in Biomedical Research: The Challenge and Response." American Medical Association White Paper (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

(56) References Cited

OTHER PUBLICATIONS

Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding A Future For Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilos et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
International Search Report and Written Opinion for International App. No. PCT/US2014/038479, dated Aug. 21, 2014, 12 pages.
International Search Report and Written Opinion for International App. No. PCT/US2015/021835, dated Sep. 16, 2015, 15 pages.
International Search Report and Written Opinion for International Application No. PCT/US2013/066248, dated Apr. 14, 2014, 28 pages.
International Search Report and Written Opinion for International Application No. PCT/US2013/066256, dated Apr. 14, 2014, 28 pages.
European Search Report for European Application No. 13159256, dated Oct. 17, 2013, 6 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005, (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping." Journal of Applied Physiology, 1991, vol. 71, No. 4, pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol, 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 60/852,787, filed Oct. 18, 2006, 112 pages.
Wittkampf et al., "Control of radiofrequency lesion size by power regulation," Journal of the American Heart Associate, 1989, 80: pp. 962-968.

(56) References Cited

OTHER PUBLICATIONS

Zheng et al., "Comparison of the temperature profile and pathological effect at unipolar, bipolar and phased radiofrequency current configurations," Journal of Interventional Cardiac Electrophysiology, 2001, pp. 401-410.
Allen, E. V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
U.S. Appl. No. 11/363,867, filed Feb. 27, 2006, 70 pp.
U.S. Appl. No. 60/813,589, filed Dec. 29, 2005, 62 pgs.
Ureter, https://en.wikipedia.org/wiki/Ureter, Jun. 2016, 6 pgs.

* cited by examiner

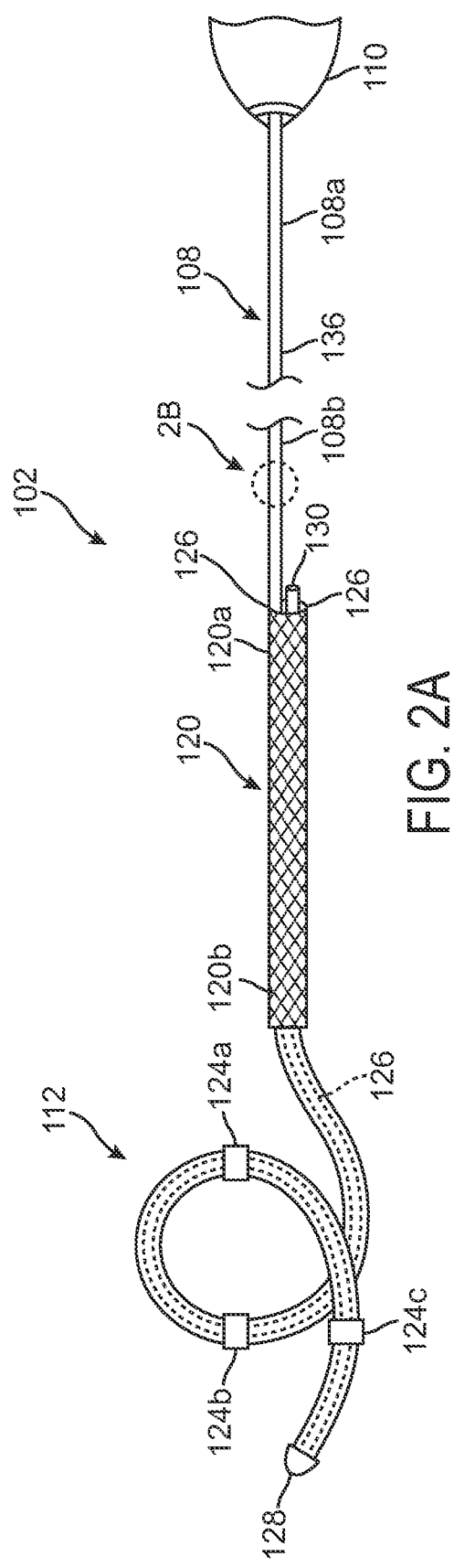
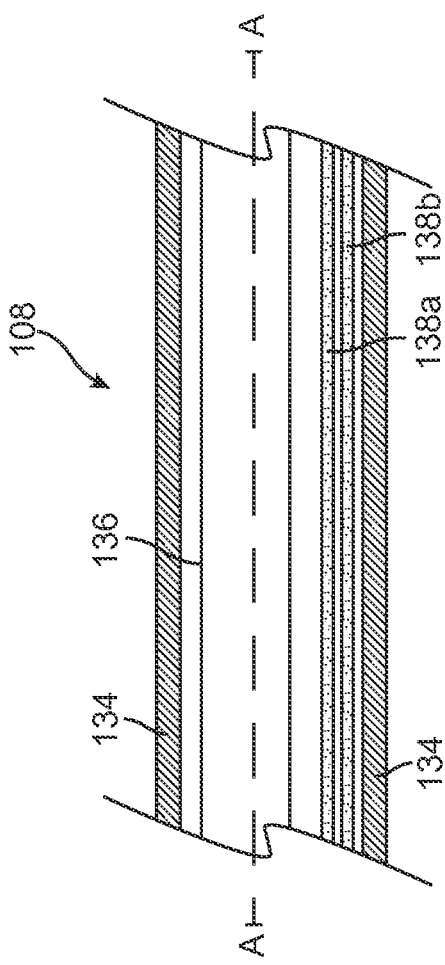
FIG. 2A
FIG. 2B

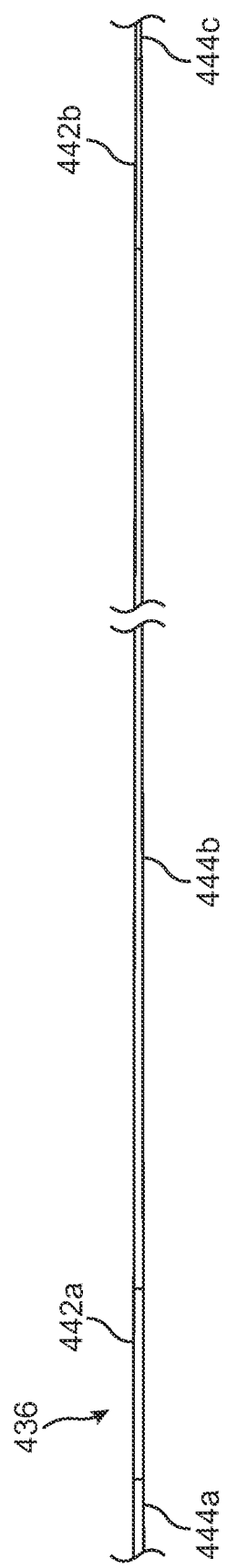

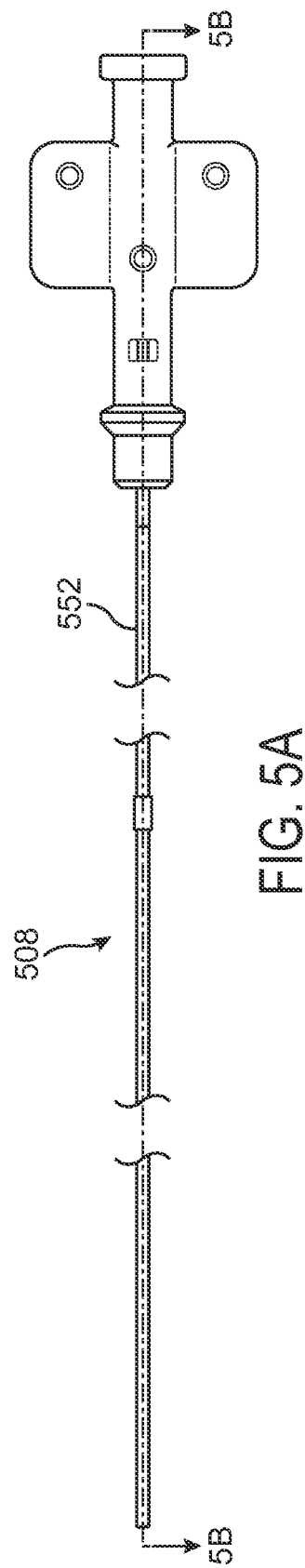
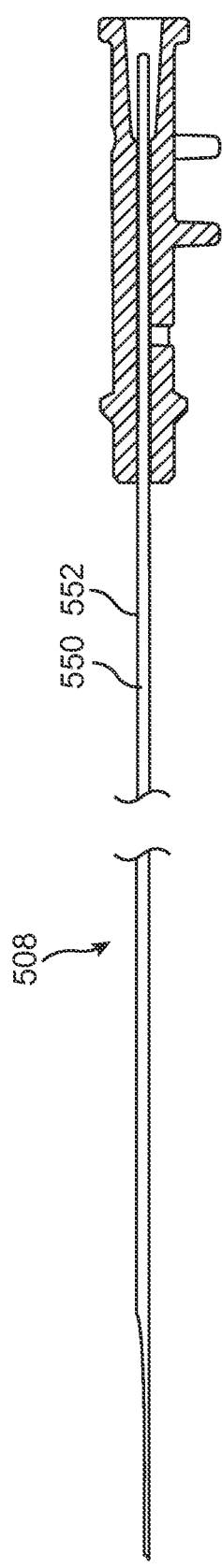
FIG. 5A
FIG. 5B

NEUROMODULATION CATHETERS WITH SHAFTS FOR ENHANCED FLEXIBILITY AND CONTROL AND ASSOCIATED DEVICES, SYSTEMS, AND METHODS

TECHNICAL FIELD

The present technology is related to neuromodulation devices. In particular, at least some embodiments are related to neuromodulation devices having mandrels and/or hypotubes that enhance flexibility and control, such as to facilitate intravascular delivery via transradial or other suitable percutaneous transluminal approaches.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIG. 2A is an enlarged side view of distal and proximal portions of the neuromodulation device shown in FIG. 1 configured in accordance with an embodiment of the present technology.

FIG. 2B is an enlarged exploded cross-sectional view of a portion of a shaft of the neuromodulation device of FIG. 2A.

FIG. 4 is a side view of a mandrel of a neuromodulation device configured in accordance with yet another embodiment of the present technology.

FIG. 5A is a side view of a shaft of a neuromodulation device configured in accordance with a further embodiment of the present technology.

FIG. 5B is a longitudinal cross-sectional view of the shaft taken along line 5B-5B of FIG. 5A.

DETAILED DESCRIPTION

Figure 1:
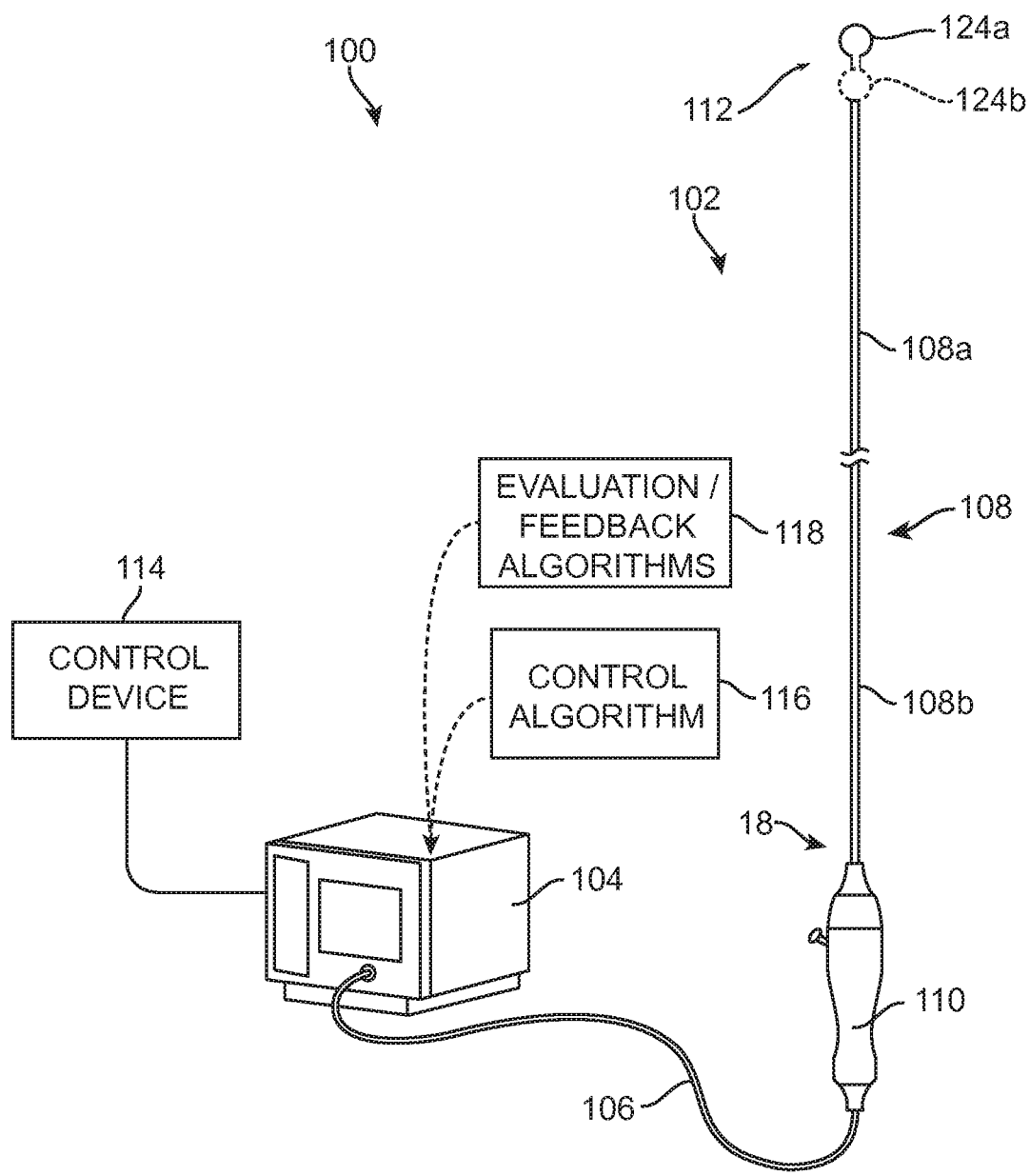
FIG. 1 is a partially schematic illustration of a therapeutic system including a neuromodulation device configured in accordance with an embodiment of the present technology.

Neuromodulation devices configured in accordance with at least some embodiments of the present technology can include a mandrel and/or a hypotube extending along at least a portion of an elongated shaft. The mandrel and/or hypotube may, for example, enhance axial stiffness (e.g., pushability or other responsiveness to axial force) and/or torsional stiffness (e.g., torqueability or other responsiveness to torsional force) without unduly compromising flexibility. For example, a neuromodulation device configured in accordance with a particular embodiment of the present technology is sufficiently flexible in some respects to facilitate deployment via a relatively long and/or tortuous intravascular path without excessive resistance, while still being sufficiently stiff in other respects so as to allow intravascular navigation or other suitable manipulation (e.g., via an extracorporeal handle). Desirable axial stiffness can include, for example, the capability of the shaft to be advanced or withdrawn along the length of an intravascular path without significantly buckling or elongating. Desirable torsional stiffness can include, for example, the capability of the shaft to distally transfer rotational motion (e.g., from a handle at a proximal end portion of the shaft to a neuromodulation assembly operably coupled to the shaft via a distal end portion of the shaft) with close correspondence (e.g., about one-to-one correspondence). Additionally or alternatively, desirable torsional stiffness can include the capability of the shaft to distally transfer rotational motion without causing wind-up that results in whipping and/or diametrical deformation of the shaft. Desirable axial and torsional stiffness together are expected to facilitate predictable and controlled transmission of axial and torsional force from the proximal end portion of the shaft toward the distal end portion of the shaft while the neuromodulation device is in use.

Neuromodulation devices configured in accordance with at least some embodiments of the present technology can be well-suited for intravascular delivery to treatment locations (e.g., treatment locations within or otherwise proximate to a renal artery of a human patient) via transradial approaches (e.g., approaches that include the radial artery, the subclavian artery, and the descending aorta) due, at least in part, to enhanced flexibility in combination with desirable axial and torsional stiffness. Transradial approaches are typically more tortuous and longer than femoral approaches and at least some other commonly used approaches. Transradial approaches may be desirable for accessing certain anatomy, but other types of approaches (e.g., femoral approaches) may be desirable in particularly tortuous anatomy or vessels having relatively small diameters. In some instances, however, use of transradial approaches can provide certain advantages over use of femoral approaches. In some cases, for example, use of transradial approaches can be associated with increased patient comfort, decreased bleeding, physician preference, and/or faster sealing of the percutaneous puncture site relative to use of femoral approaches.

In addition to or instead of facilitating intravascular delivery via transradial approaches, neuromodulation devices configured in accordance with at least some embodiments of the present technology can be well suited for intravascular delivery via one or more other suitable approaches, such as other suitable approaches that are shorter or longer than transradial approaches and other suitable approaches that are less tortuous or more tortuous than transradial approaches. For example, neuromodulation devices configured in accordance with at least some embodiments of the present technology can be well suited for intravascular delivery via brachial approaches and/or femoral approaches. Even when used with approaches that are generally shorter and/or less tortuous than transradial approaches, the combination of flexibility in bending and desirable axial and torsional stiffness associated with neuromodulation devices configured in accordance with at least some embodiments of the present technology can be beneficial, such as to accommodate anatomical differences between patients and/or to reduce vessel trauma during delivery, among other potential benefits.

Specific details of several embodiments of the present technology are described herein with reference to FIGS. 1-9B. Although many of the embodiments are described herein with respect to devices, systems, and methods for intravascular renal neuromodulation, other applications and other embodiments in addition to those described herein are within the scope of the present technology. For example, at least some embodiments may be useful for intraluminal neuromodulation, for extravascular neuromodulation, for non-renal neuromodulation, and/or for use in therapies other than neuromodulation. It should be noted that other embodiments in addition to those disclosed herein are within the scope of the present technology. For example, in still other embodiments, the technology described herein may be used in devices, systems and methods for stent delivery and balloon angioplasty. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation device). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

I. Selected Examples of Neuromodulation Devices and Related Systems

FIG. 1 is a partially schematic illustration of a therapeutic system 100 ("system 100") configured in accordance with an embodiment of the present technology. The system 100 can include a neuromodulation device 102 (e.g., a neuromodulation catheter), a console 104, and a cable 106 extending therebetween. The neuromodulation device 102 can include an elongated shaft 108 having a proximal end portion 108a and a distal end portion 108b. As explained in further detail below, a mandrel can define the shaft 108 or a portion thereof. A handle 110 of the neuromodulation device 102 can be operably connected to the shaft 108 via the proximal end portion 108a, and a neuromodulation assembly 112 can be operably connected to the shaft 108 via the distal end portion 108b. The neuromodulation assembly 112 can include one or more energy delivery elements (identified individually as a first energy delivery element 124a and a second energy delivery element 124b, and referred to collectively as energy delivery elements 124), such as a plurality of electrodes. For example, in certain embodiments the neuromodulation assembly 112 can include a single-electrode configuration, such as that described in International Patent Application No. PCT/US2009/069334 (international Patent Application Publication No. WO 2010/078175), filed Dec. 22, 2009, which is incorporated herein by reference in its entirety, in the illustrated embodiment, the second energy delivery element 124b is illustrated in broken lines to indicate that the systems and methods disclosed herein can be used with neuromodulation devices having one or more energy delivery elements 124. Further, it will be appreciated that although only two energy delivery elements 124 are shown, the neuromodulation device 102 may include additional energy delivery elements 124 (e.g., four electrodes, five electrodes, six electrodes, etc.). For example, the neuromodulation assembly 112 can be configured to have a spiral/helical shape with a plurality of energy delivery elements 124 positioned thereon. The spiral/helical shape may be at least partially straightened by a guide wire for delivery to a target site over the guide wire. Once the neuromodulation assembly 112 is at or near the target site, the guide wire may be at least partially proximally withdrawn to thereby allow the neuromodulation assembly 112 to reassume its spiral/helical shape. Examples of suitable multi-electrode neuromodulation assemblies 112 are described in U.S. patent application Ser. No. 13/281,360, filed Oct. 25, 2011, and U.S. patent application Ser. No. 13/793,647, filed Mar. 11, 2013, each of which is incorporated herein by reference in its entirety. In further embodiments, shaft 108 can be incorporated with neuromodulation assemblies having different structural configurations and/or may include one or more energy delivery elements 124 other than electrodes. For example, the shaft 108 can be incorporated with neuromodulation assemblies disclosed in International Patent Application No. PCT/US2011/057153 (International Patent Application Publication No. WO2012/054862), U.S. patent application Ser. No. 13/826,604, U.S. patent application Ser. No. 12/940,922 (U.S. Patent Publication No. 2011/0112400), International Patent Application No. PCT/US2011/057514, and U.S. patent application Ser. No. 13/458,859, each of which is incorporated herein by reference in its entirety.

The shaft 108 can be configured to locate the neuromodulation assembly 112 intravascularly at a treatment location within or otherwise proximate to a body lumen (e.g., a blood vessel, a duct, an airway, or another naturally occurring lumen within the human body), and the neuromodulation assembly 112 can be configured to provide or support a neuromodulation treatment at the treatment location (e.g., a treatment site within the renal arteries). The shaft 108 and the neuromodulation assembly 112 can be 2, 3, 4, 5, 6, or 7 French or one or more other suitable sizes.

In some embodiments, intravascular delivery of the neuromodulation device 102 includes percutaneously inserting a guide wire (not shown) into a body lumen of a patient and moving the shaft 108 and the neuromodulation assembly 112 along the guide wire until the neuromodulation assembly 112 reaches a suitable treatment location (e.g., a renal artery). In certain embodiments, for example, the distal end of the neuromodulation assembly 112 may define a passageway for engaging a guide wire (not shown) for delivery of the neuromodulation assembly 112 using over-the-wire ("OTW") or rapid exchange ("RX") techniques. In other embodiments, the neuromodulation device 102 can be a steerable or non-steerable device configured for use without a guide wire. In still other embodiments, the neuromodulation device 102 can be configured for delivery via a guide catheter or sheath (not shown).

The console 104 can be configured to control, monitor, supply, and/or otherwise support operation of the neuromodulation device 102. Alternatively, the neuromodulation device 102 can be self-contained or otherwise configured for operation without connection to the console 104. When present, the console 104 can be configured to generate a selected form and/or magnitude of energy for delivery to tissue at the treatment location via the neuromodulation assembly 112 (e.g., via the energy delivery elements 124). The console 104 can have different configurations depending on the treatment modality of the neuromodulation device 102. When the neuromodulation device 102 is configured for electrode-based, heat-element-based, or transducer-based treatment, for example, the console 104 can include an energy generator (not shown) configured to generate radio frequency (RF) energy (e.g., monopolar and/or bipolar RF energy), pulsed energy, microwave energy, optical energy, ultrasound energy (e.g., intravascularly delivered ultrasound, high-intensity focused ultrasound (HIFU), and/or other types of ultrasound), cryotherapeutic energy, direct heat energy, chemicals (e.g., drugs and/or other agents), radiation (e.g., infrared, visible, and/or gamma radiation), and/or another suitable type of energy. When the neuromodulation device 102 is configured for cryotherapeutic treatment, the console 104 can include a refrigerant reservoir (not shown) and can be configured to supply the neuromodulation device 102 with refrigerant. Similarly, when the neuromodulation device 102 is configured for chemical-based treatment (e.g., drug infusion), the console 104 can include a chemical reservoir (not shown) and can be configured to supply the neuromodulation device 102 with one or more chemicals.

In some embodiments, the system 100 includes a control device 114 communicatively coupled to the neuromodulation device 102. The control device 114 can be configured to initiate, terminate, and/or adjust operation of one or more components of the neuromodulation device 102 directly and/or via the console 104. In other embodiments, the control device 114 can be omitted or have other suitable locations (e.g., within the handle 110, along the cable 106, etc.). The console 104 can be configured to execute an automated control algorithm 116 and/or to receive control instructions from an operator. Further, the console 104 can be configured to provide feedback to an operator before, during, and/or after a treatment procedure via an evaluation/feedback algorithm 118.

FIG. 2A is an enlarged side view of distal and proximal portions of the neuromodulation device 102 of FIG. 1 configured in accordance with an embodiment of the present technology. As shown in FIG. 2A, the shaft 108 can extend proximally from a proximal portion 120a of a transition member 120, and the neuromodulation assembly 112 can extend distally from a distal portion 120b of the transition member 120. As explained in further detail below, the shaft 108 includes a solid-core mandrel 136 extending through at least a portion of its length to increase the axial and/or torsional stiffness of the shaft 108, while still maintaining sufficient flexibility to navigate the shaft 108 through tortuous anatomy. In the illustrated embodiment, the distal end portion 108b of the shaft 108 can be attached to the proximal portion 120a of the transition member 120 at an attachment site via an adhesive bond and/or other suitable types of attachment mechanisms (e.g., sutures, welding, etc.) This proximally-positioned attachment site may be referred to as a "conversion bond" or "exchange bond" as it is located proximate to the transition to the distal-most section of the neuromodulation device 102. As explained in further detail below, in other embodiments the shaft 108 can extend through at least a portion of the transition member 120 to further enhance the axial and/or torsional control the operator has over the neuromodulation assembly 112.

The transition member 120 can be made from a low-profile braided material that is configured to increase the stability and control at the junction between the shaft 108 and the neuromodulation assembly 112. The braided material, for example, can be made from para-aramid synthetic fiber sold under the trademark KEVLAR, polyether ether ketone (PEEK) polymer, and/or other suitable materials that enhance the stability of the transition member 120. The overall length of the transition member 120 can be about 5-25 cm (1.97-9.84 inches) (e.g., 10 cm (3.94 inches), 15 cm (5.91 inches), 20 cm (7.87 inches), etc.) depending upon the desired level of control, stiffness, and/or other suitable properties. In other embodiments, the transition member 120 can have other suitable lengths and/or can be made from other suitable materials (e.g., non-braided polymer tubing). In further embodiments, the transition member 120 may be omitted, and the distal end portion 108b of the shaft 108 can be integrally formed with or attached to the neuromodulation assembly 112.

As shown in FIG. 2A, the neuromodulation assembly 112 can include a guide wire channel or lumen 126 extending along its length and proximally through the transition member 120. The guide wire lumen 126 has a distal opening 128 at a distal end portion of the neuromodulation assembly 112 and a proximal opening 130 proximate to the proximal portion 120a of the transition member 120. Accordingly, the neuromodulation assembly 112 can be threaded over a guide wire (not shown), and the guide wire can extend proximally from the transition member 120. This configuration facilitates delivery to a treatment site using RX delivery techniques because the guide wire only extends through a portion of the neuromodulation device 102 (rather than along the entire length of the shaft 108).

In the embodiment illustrated in FIG. 2A, the neuromodulation assembly 112 has a spiral shape with a plurality of energy delivery elements 124 (identified individually as first through third energy delivery elements 124a-c, respectively) spaced apart from one another along the length of the neuromodulation assembly 112. The energy delivery elements 124 can be electrodes, transducers, and/or other types of energy delivery elements suitable for modulation of neural fibers. In other embodiments, the neuromodulation assembly 112 can include fewer or more than three energy delivery elements 124, and/or have other suitable shapes or arrangements.

FIG. 2B is an enlarged exploded cross-sectional view of a portion of the shaft 108 of FIG. 2A configured in accordance with an embodiment of the present technology. The shaft 108 includes the solid-core mandrel 136 and a plurality of energy delivery wires (identified individually as first and second energy delivery wires 138a and 138b, respectively, and referred to collectively as mew delivery wires 138) disposed within an outer covering/sheath or wall 134 and extending along a longitudinal axis A-A of the shaft 108. The mandrel 136 may be disposed along the entire length of the shaft 108 (e.g., from the proximal end portion 108a to the distal end portion 108b (FIG. 1)), or may extend through only a portion of the shaft 108 (e.g., a predetermined distance from the distal end portion 108b of the shaft 108, a predetermined distance from the proximal end portion 108a of the shaft 108, through an intermediate portion of the shaft 108, etc.). In various embodiments, the mandrel 136 can have a substantially constant outer diameter along the length of the shaft 108. In other embodiments (such as the embodiments described below with reference to FIG. 3), the diameter of the mandrel 136 may differ along longitudinal segments of the shaft 108.

The mandrel 136 can provide axial stiffness (e.g., pushability or other responsiveness to axial force) and/or torsional stiffness (e.g., torqueability or other responsiveness to torsional force) to the shaft 108 without compromising flexibility. For example, the mandrel 136 can be made of a relatively strong material (e.g., nitinol, stainless steel, or other suitable metals) having an outer diameter of for example, about 0.051-0.076 cm (0.02-0.03 inch) (e.g., 0.956 cm (0.022 inch), 0.051 cm (0.024 inch), 0.071 cm (0.028 inch), etc.). Such mandrels have been shown to exhibit greater flexibility (e.g., as determined by a three point bending flexural test) than hypotubes (e.g., hypotubes having an outer diameter of 0.081 cm (0.32 inch) and an inner diameter of 0.063 cm (0.025 inch)). The enhanced flexibility and increased control of pushability (e.g., axial stiffness) and torqueability (e.g., torsional stiffness) provided by the mandrel 136 can facilitate delivery of the neuromodulation assembly 112 (FIG. 2A) to a treatment site via tortuous intravascular paths (e.g., a transradial approach to a renal artery of a human patient). In addition, the increased flexibility and control provided by the mandrel 136 is not expected to unduly increase the overall outer diameter of the shaft 108. For example, in several embodiments the neuromodulation device 102 (FIGS. 1 and 2A) can be introduced via a 5F guide catheter. In other embodiments, the neuromodulation device 102 can be percutaneously introduced into the body using larger or smaller introducer devices.

In various embodiments, longitudinal segments of the mandrel 136 can be configured to have varying flexibilities, axial and/or torsional stiffnesses, and/or other physical properties. For example, heat treatments can be applied to discrete sections of the mandrel 136 to change (e.g., optimize) flexibility of certain portions of the mandrel 136. It is expected that annealing discrete longitudinal segments of the mandrel 136 will change the molecular structure of the mandrel material to make the annealed segment more flexible (e.g., less resistant to deflection in response to lateral force), whereas cold working (e.g., drawing and quenching) discrete segments of the mandrel 136 is expected to change the molecular structure to make the mandrel 136 stiffer. In other embodiments, different or additional processes can be applied to longitudinal segments of the mandrel 136 to change desired physical properties of the material. As described in further detail below with reference to FIG. 3, in some embodiments the outer diameter of longitudinal segments of the mandrel 136 can be varied (e.g., tapered) to increase/decrease the flexibility of certain portions of the mandrel 136. Accordingly, portions of the mandrel 136 can be configured to have varying degrees of flexibility (e.g., to facilitate intravascular delivery of a neuromodulation assembly to a treatment location within or otherwise proximate to a renal artery of a human patient via a transradial or other suitable approach).

As further shown in FIG. 2B, the energy delivery wires 138 can extend through the length of the shaft 108 along the side of the mandrel 136. The energy delivery wires 138 can be operably coupled to the energy delivery elements 124 (FIG. 2A) at a distal end of the neuromodulation device 102, and an energy delivery device (e.g., the console 104 of FIG. 1) coupled to a proximal end of the neuromodulation device 102 and external to a patient. In other embodiments, the energy delivery wires 138 can be arranged in other suitable configurations along the length of the shaft 108. For example, the energy delivery wires 138 can be wrapped around the mandrel 136 in a helical pattern. In certain embodiments, one energy delivery wire 138 can delivery energy to an energy delivery element 124 (FIG. 2A), and the other energy delivery wire 138 can detect temperature proximate to the treatment site. In other embodiments, each energy delivery wire 138 can correspond to an individual energy delivery element 124 (FIG. 2A) of the neuromodulation assembly 112 to provide for independent control of the energy delivery elements 124. In further embodiments, the shaft 108 can include other types of wires configured to provide heat-element-based or transducer-based treatment via the neuromodulation assembly 112 (e.g., cryotherapeutic treatment, direct heat treatment, etc.). The shaft 108 can additionally or alternatively include additional wires or lines for detecting various parameters at the treatment site and/or otherwise associated with operation of the neuromodulation device 102.

The energy delivery wires 138, mandrel 136, and other components of the shaft 108 can be encapsulated by the outer wall 134 to electrically insulate and protect the elements from the external environment. The outer wall 134 can be made from a thin layer of polymer material, e.g., with a thickness of about 0.025-0.003 cm (0.01-0.001 inch), and formed using an overjacketing process (e.g., overjacketing extrusion) in which the mandrel 136 and other elements extending along the shaft 108 (e.g., the energy delivery wires 138) are pulled through the center of a die. In other embodiments, the outer wall 134 can be made from other electrically isolative materials suitable for encapsulating the mandrel 136 and other shaft elements and suitable for insertion into a human patient.

Figure 3:
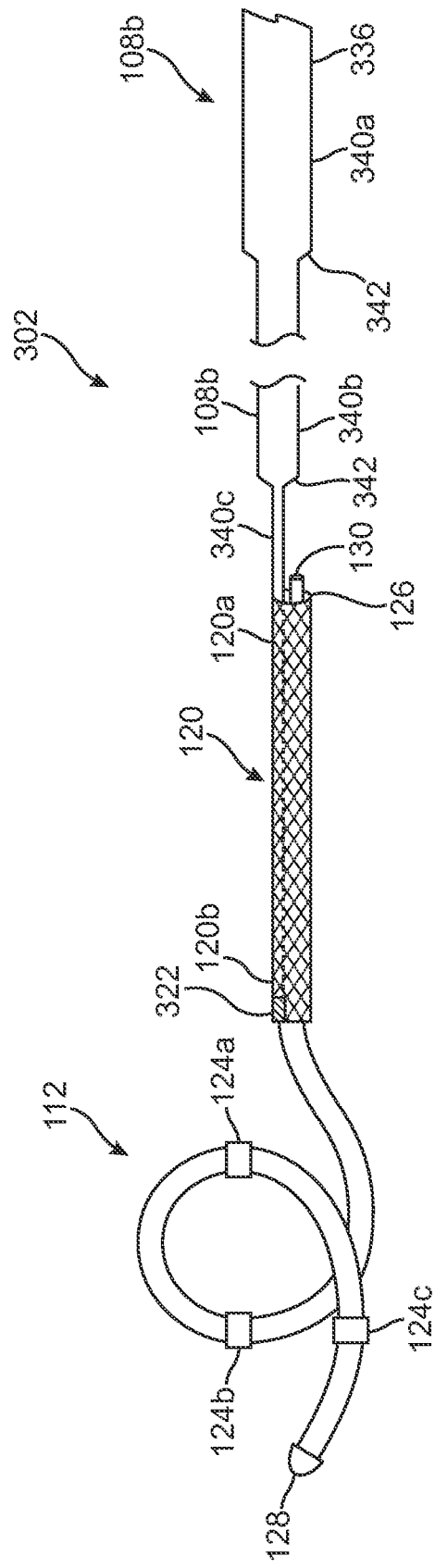
FIG. 3 is a side view of a distal portion of a neuromodulation device configured in accordance with another embodiment of the present technology.

FIG. 3 is an enlarged partial side view of a distal portion of a neuromodulation device 302 configured in accordance with another embodiment of the present technology. The neuromodulation device 302 can include several features generally similar in structure and/or function as the features of the neuromodulation device 102 described above with respect to FIGS. 1-2B. For example, the neuromodulation device 302 includes the elongated shaft 108 with the distal end portion 108b operably coupled to a neuromodulation assembly 112 and the transition member 120 with the guide wire lumen 126 to facilitate RX guide wire delivery of the neuromodulation assembly 112 to a treatment site. The neuromodulation device 302 further includes a mandrel 336 (e.g., encased in a polymer overjacket) extending along at least a portion of the elongated shaft 108. Similar to the mandrel 136 described above with respect to FIGS. 2A and 2B, the mandrel 336 of FIG. 3 can enhance the axial and/or torsional stiffness of the shaft 108 without compromising the flexibility of the shaft 108 and, therefore, facilitate delivery of the neuromodulation assembly 112 to a treatment site along tortuous intravascular paths (e.g., transradial delivery to the renal arteries).

As shown in FIG. 3, the mandrel 336 includes a plurality of stepped longitudinal segments or portions (identified individually as first to third stepped portions 340a-c, respectively, and referred to collectively as stepped portions 340) that have decreasingly smaller outer diameters toward the distal end of the shaft 108. In the illustrated embodiment, the mandrel 336 includes three stepped portions 340 and tapered transition regions 342 between each stepped portion 340 (e.g., formed using a sandless grinding process, laser cutting, etc.). In other embodiments, the mandrel 336 may include two stepped portions 340, more than three stepped portions 340, and/or the transition regions 342 may have different configurations (e.g., a hard step between each stepped portion 340).

Decreasing the diameter of the mandrel 336 relates to an increase in the flexibility of the mandrel 336. Referring to FIG. 3, for example, the third stepped portion 340c has the smallest outer diameter and, therefore, is more flexible than the first and second stepped portions 340a and 340b. Accordingly, the outer diameter of longitudinal segments of the mandrel 336 can be selected to provide varying degrees of flexibilities at specific portions of the mandrel 336. In other embodiments, the mandrel 336 can have a continuous taper along its entire length (e.g., using laser cutting techniques) or along discrete portions of the mandrel 336 to gradually increase the flexibility of the mandrel 336 toward the distal or proximal end. In further embodiments, the mandrel 336 can include other structural features that alter the flexibility of discrete portions of the mandrel 336.

As further illustrated in FIG. 3, the mandrel 336 can extend through at least a portion of the transition member 120 and can be attached at a bond site 322 proximate to the distal portion 120b of the transition member 120. In other embodiments, the mandrel 336 can extend to an intermediate portion of the transition member 120. This elongated mandrel 336 can increase the push and/or torsional efficiency of the shaft 108 by providing enhanced axial and/or torsional stiffness along the transition member 120. As shown in FIG. 3, the mandrel 336 can be tapered to a small outer diameter so as not to substantially increase the overall diameter of the transition member 120 and, therefore, facilitate low-profile intravascular delivery to a treatment site with increased distal control.

FIG. 4 is a side view of a mandrel 436 of a neuromodulation device (e.g., the neuromodulation device 102 described above) configured in accordance with yet another embodiment of the present technology. The mandrel 436 can define at least a portion of the shaft of the neuromodulation device. For example, the mandrel 436 can define a proximal portion of the shaft extending from a handle to a transitional or intermediate shaft, which in turn connects to a neuromodulation assembly. Similar to the transition member 120 described above, the intermediate shaft can be made of a braided polymer and transition the shaft from the mandrel 436 to the neuromodulation assembly (e.g., for RX-type guidewire delivery). In certain embodiments, the mandrel 436 can have a length of about 130-160 cm (51-63 inches) (e.g., 152 cm (60 inches)) to allow the mandrel 436 to extend through a substantial portion of a patient's vasculature (e.g., from a radial artery insertion site, through the arteries of the upper limb to the descending aorta). In other embodiments, the mandrel 436 may be longer or shorter depending on various factors, such as the patient's anatomy and/or the navigation path of the shaft, and/or the mandrel 436 may extend along different portions of the shaft. Similar to the mandrels 136 and 336 described above, the mandrel 436 of FIG. 4 can have a solid core, and can be encased in a polymer overjacket.

The mandrel 436 can have differently sized outer diameters along longitudinal portions of the mandrel 436, and the outer diameters of the longitudinal portions may decrease toward the distal end of the mandrel 436. In the embodiment illustrated in FIG. 4, for example, the mandrel 436 includes two tapered sections or zones (identified individually as a first tapered zone 442a and a second tapered zone 442b, and referred to collectively as tapered zones 442) that separate longitudinal segments (identified individually as a proximal longitudinal segment 444a, an intermediate longitudinal segment 444b, and a distal longitudinal segment 444c, and referred to collectively as longitudinal segments 444) of the mandrel 436. Each longitudinal segment 444 can have a different outer diameter, with the proximal longitudinal segment 444a having the largest outer diameter, the distal longitudinal segment 444c having the smallest outer diameter, and the intermediate longitudinal segment 444b having an outer diameter scaled between the outer diameters of the proximal and distal longitudinal segments 444a and 444c. For example, the proximal longitudinal segment 444a can have an outer diameter of about 0.4-0.8 min (0.016-0.031 inch) (e.g., 0.510 min (0.020 inch)), the distal longitudinal segment 444c can have outer diameter of about 0.1-0.4 mm (0.004-0.016 inch) (e.g., 0.254 mm (0.010 inch)), and the intermediate longitudinal segment 444b can have outer diameter of about 0.3-0.6 mm (0.012-0.024 inch) (e.g., 0.457 mm (0.018 inch)). This configuration is expected to provide increased flexibility toward the distal end of the mandrel 436. In various embodiments, for example, the distal longitudinal segment 444c with its small outer diameter can extend at least partially into an intermediate shaft portion (e.g., the transition member 120 described above) to provide a smooth transition in bending stiffness at the exchange joint (i.e., between the proximal portion of the shaft and the intermediate portion of the shaft).

As shown in FIG. 4, the tapered zones 442 can have a constant taper from the outer diameter of one longitudinal segment 444 to the adjacent longitudinal segment 444. The tapered zones 442 can be formed by grinding and/or other suitable manufacturing techniques. In certain embodiments, each tapered zone 442 can have a length of about 3-16 mm (0.12-0.63 inch) (e.g., 9.906 mm (0.390 inch)). In other embodiments, however, the tapered zones 442 can be longer or shorter and/or the individual tapered zones 442 can have differing lengths.

The tapered mandrel 436 is expected to enhance the trackability of the shaft by tuning the mandrel's flexibility for navigating selected portions within the anatomy. For example, the distal portion of the mandrel 436 may be required to extend through more tortuous portions of the vasculature (e.g., small vessels) than the intermediate or proximal portions of the mandrel 436, and therefore the length and the outer diameter of the distal longitudinal segment 444c can be selected to provide sufficient flexibility for its specific application. Similarly, the outer diameters and lengths of the intermediate and proximal longitudinal segments 444b and 444a can be selected based the portions of the vasculature they are intended to navigate. In other embodiments, the mandrel 436 can include more than three or fewer than three longitudinal segments 444 with differing outer diameters and/or lengths to provide the desired flexibility throughout the shaft for a specific application.

Figure 5C:
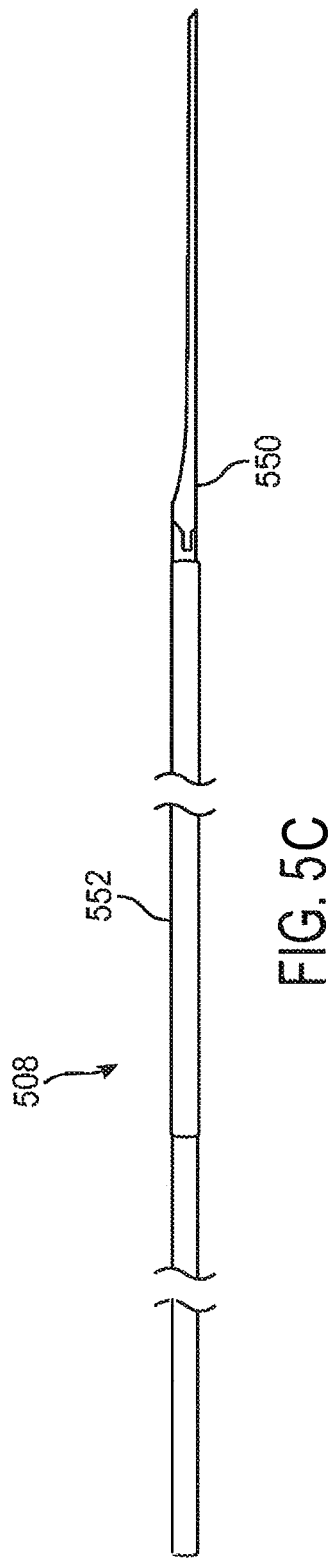
FIG. 5C is an enlarged view of a distal portion of the shaft of FIGS. 5A and 5B.

FIG. 5A is a side view of a portion of a shaft 508 of a neuromodulation device (e.g., the neuromodulation device 102 described above) configured in accordance with a further embodiment of the present technology. FIG. 5B is a longitudinal cross-sectional view of the shaft 508 taken along line 5B-5B of FIG. 5A, and FIG. 5C is an enlarged view of a distal section of the shaft 508 of FIGS. 5A and 5B. Referring to FIGS. 5A-5C together, the shaft 508 can include a hypotube 550 (FIG. 5B) that extends along at least a proximal portion of the shaft 508 and an outer jacket 552 (e.g., a polymer overjacket) at least partially encasing the hypotube 550. For example, the hypotube 550 can extend through about two thirds of the length of the shaft 508 (e.g., about 101-154 cm (40-60 inches)). In other embodiments, however, the hypotube 550 can extend through longer or shorter portions of the shaft 508. As shown in FIG. 5C, the hypotube 550 can extend distally from the outer jacket 552 and have a tapered or oblique opening (e.g., about 0.500 cm (0.20 inch) in length) such that the hypotube 550 thins to a semi-circular structure (e.g., about 2.0 cm (0.80 inch) in length). In certain embodiments, for example, the distal exposed portion of the hypotube 550 can be about 2-4 cm (0.80-1.6 inches) (e.g., 2.2 cm (0.866 inch)) in length. This distal end portion may extend into an intermediate shaft portion (e.g., the transition member 120 described above), connect directly to a neuromodulation assembly at the distal end of the shaft 508, and/or attach to another portion of the shaft 508.

Figure 5D:
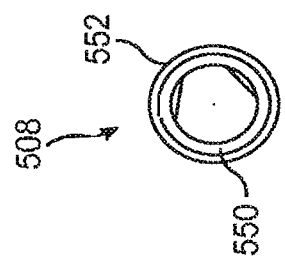
FIG. 5D is a cross-sectional view of the shaft of FIGS. 5A-5C.

Referring to FIG. 5D, in one particular embodiment, the outer diameter of the shaft 508 (e.g., the outer diameter of the outer jacket 552) can be about 0.75-1.5 mm (0.03-0.06 inch) (e.g., 0.914 mm (0.036 inch)), the outer diameter of the hypotube 550 can be about 0.5-1.0 mm (0.02-0.04 inch) (e.g., 0.813 mm (0.032 inch)), and the inner diameter of the hypotube 550 can be about 0.3-0.75 mm (0.01-0.03 inch) (e.g., 0.635 mm (0.025 inch)). The inner diameter of the hypotube 550 can be selected to house various components of the neuromodulation device (e.g., electrical wires) and/or allow for instrument throughput. For example, the hypotube 550 can provide a lumen through which a guidewire can be extended to facilitate delivery of the shaft 508 to a treatment site within the vasculature of a human patient and/or facilitate deployment of a neuromodulation assembly at a distal portion of the shaft 508. In other embodiments, the outer jacket 552 and/or the hypotube 550 can have other suitable dimensions.

In some embodiments, the hypotube 550 can be made from nitinol and laser cut to the desired configuration. A nitinol hypotube is expected to provide enhanced torque control relative to a number of conventional stainless steel hypotubes by having sufficient torsional stiffness while its stress induced martensite (SIM) property provides superelasticity for a high degree of kink resistance to navigate through tortuous vasculature. In other embodiments, the hypotube 550 can be made from other suitable materials that impart trackability to the shaft 508 without compromising flexibility.

In various embodiments, the hypotube 550 or portions thereof can be formulated and/or heat treated or otherwise prepared or tuned to provide desired characteristics, such as a specific degree of flexibility. For example, a distal portion of the hypotube 550 (e.g., having a length of about 50 cm (19.69 inches)) can be tuned (e.g., heat treated) so that it is highly flexible at body temperature (i.e., about 37° C.), and is therefore suited for intravascular delivery or other operations within the body. Nitinol, for example, can be formulated and/or prepared to have an austenite finish temperature ($A_f$) suited for operation at body temperature. Accordingly, a distal portion of the nitinol hypotube 550 can be tuned to have a desired flexibility and SIM capability at body temperature to enhance its performance through tortuous anatomy (e.g., the portion of a transradial access route to the renal arteries that extends through the subclavian artery), and the proximal portion of the hypotube 550 can remain more stiff in an austenite phase. In other embodiments, longitudinal segments of the hypotube 550 can be tuned to have other desired material properties depending on the specific application.

II. Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment locations during a treatment procedure. The treatment location can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment location in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

III. Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 6:
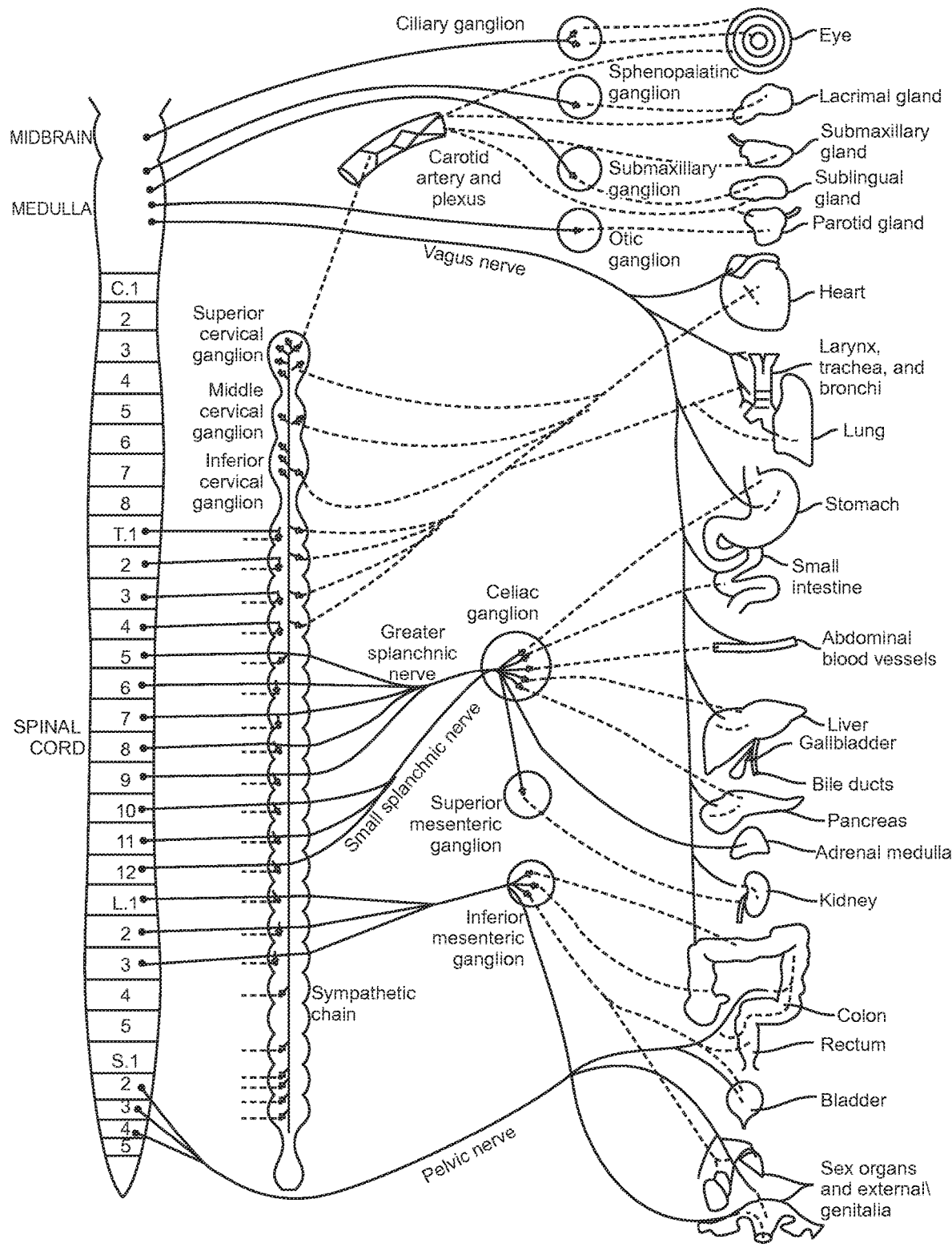
FIG. 6 is a conceptual illustration of the sympathetic nervous system (SNS) and how the brain communicates with the body via the SNS.

As shown in FIG. 6, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 7:
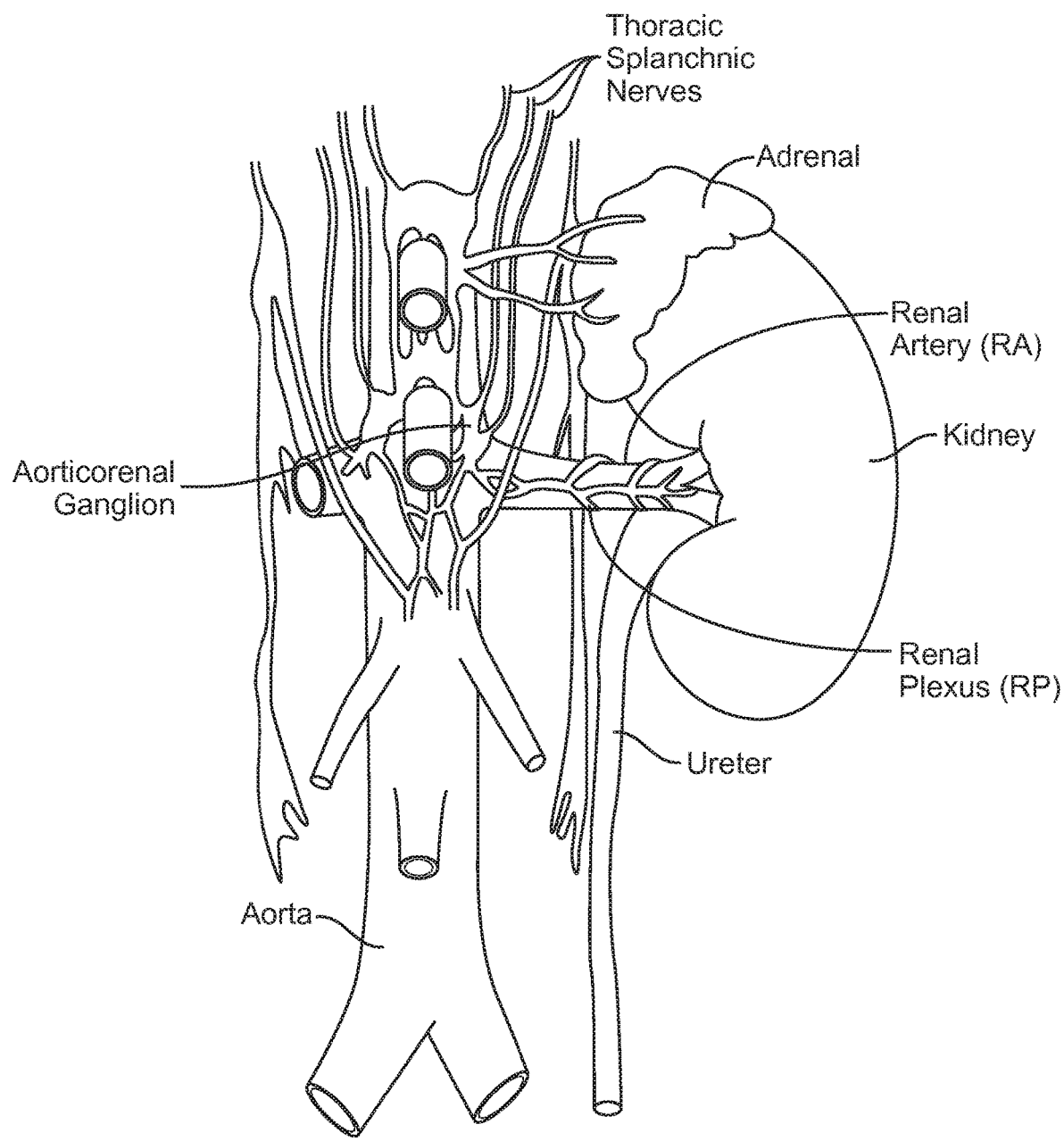
FIG. 7 is an enlarged anatomic view of nerves innervating a left kidney to form the renal plexus surrounding the left renal artery.

As FIG. 7 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 8A:
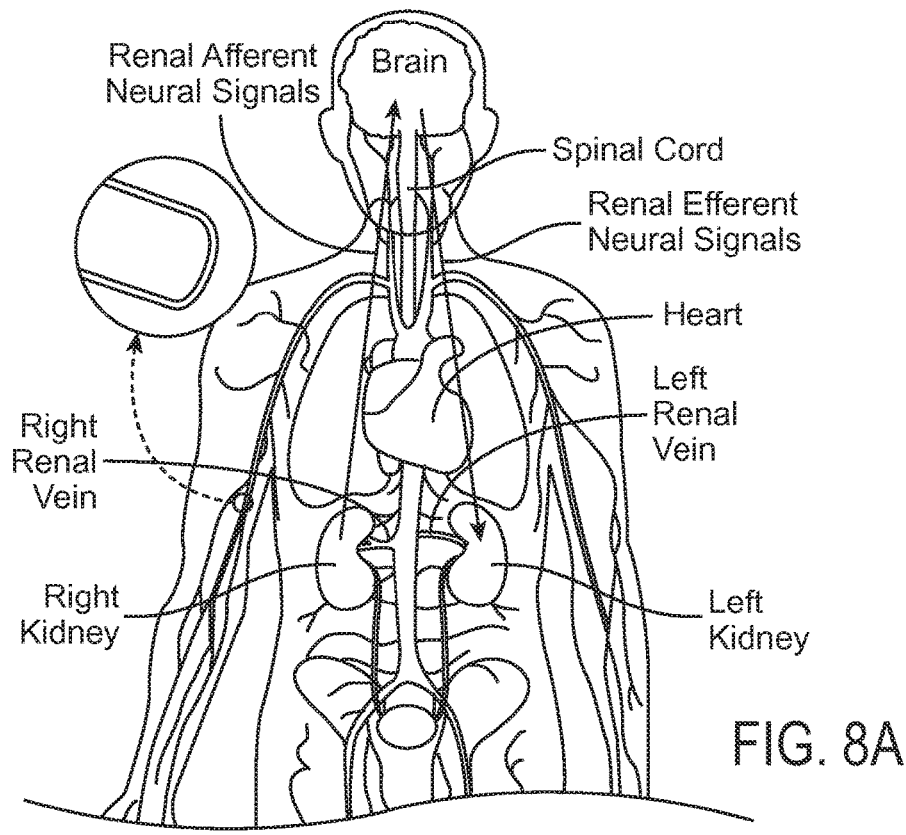
FIGS. 8A and 8B are anatomic and conceptual views, respectively, of a human body depicting neural efferent and afferent communication between the brain and kidneys.
Figure 8B:
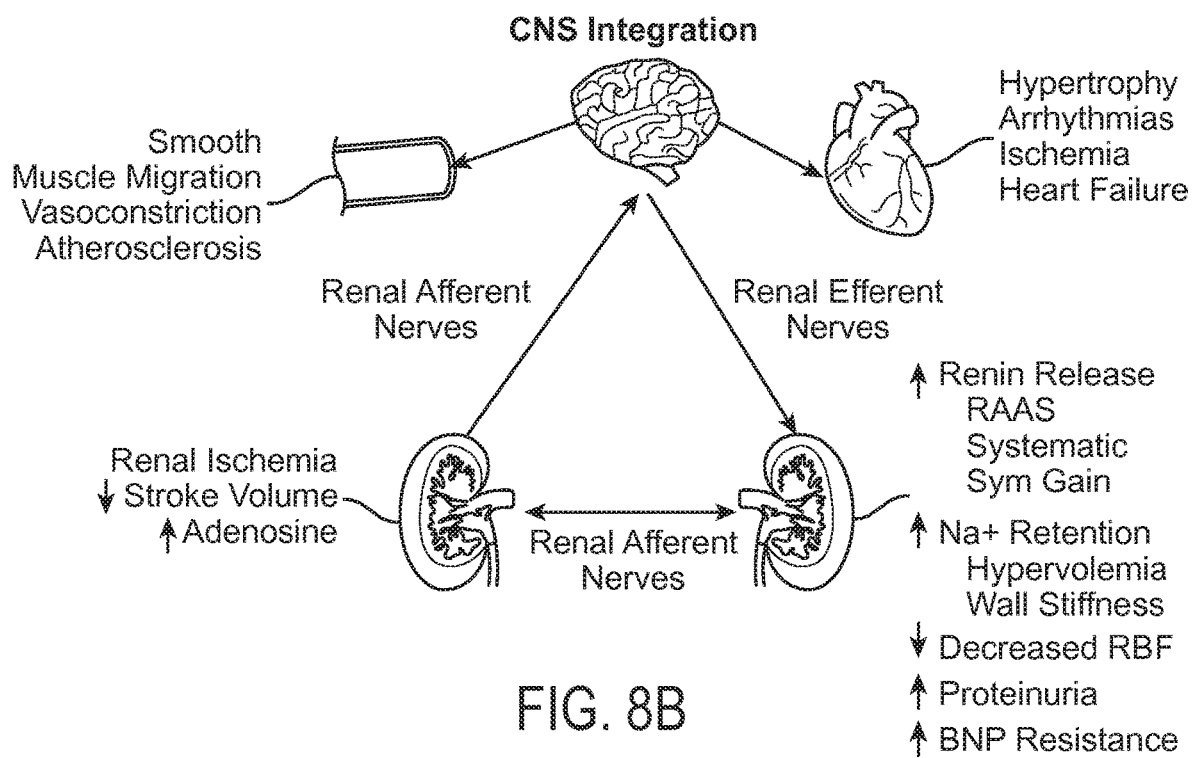

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 8A and 8B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 6. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 9A:
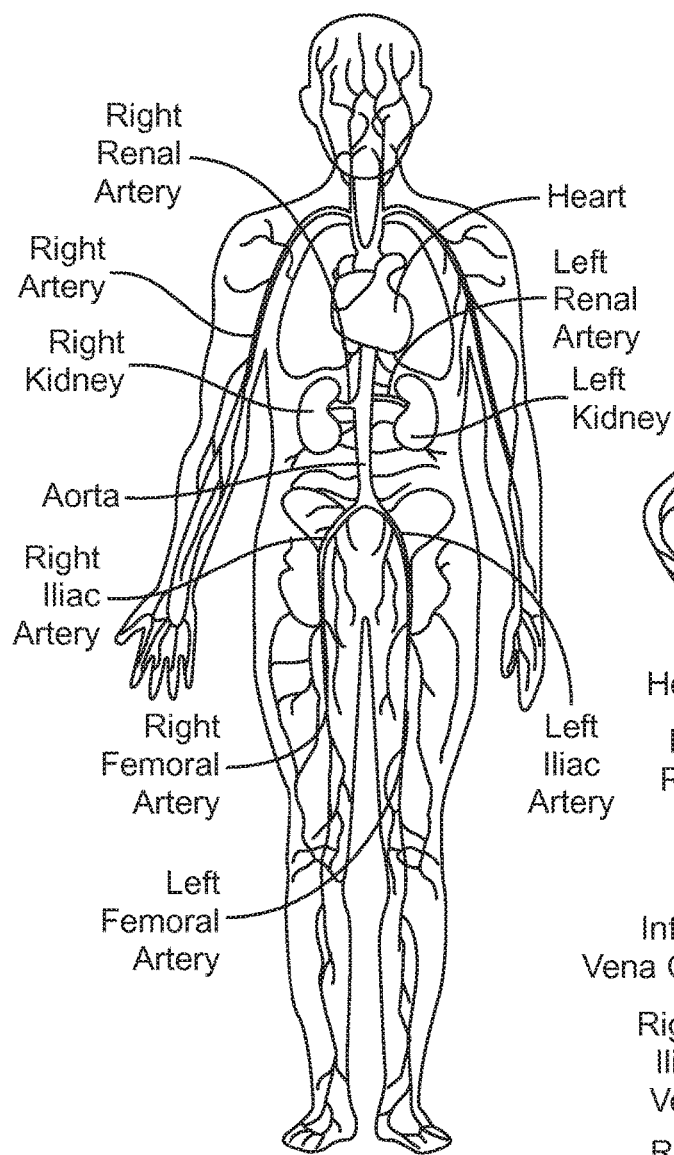
FIGS. 9A and 9B are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 9A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 9B:
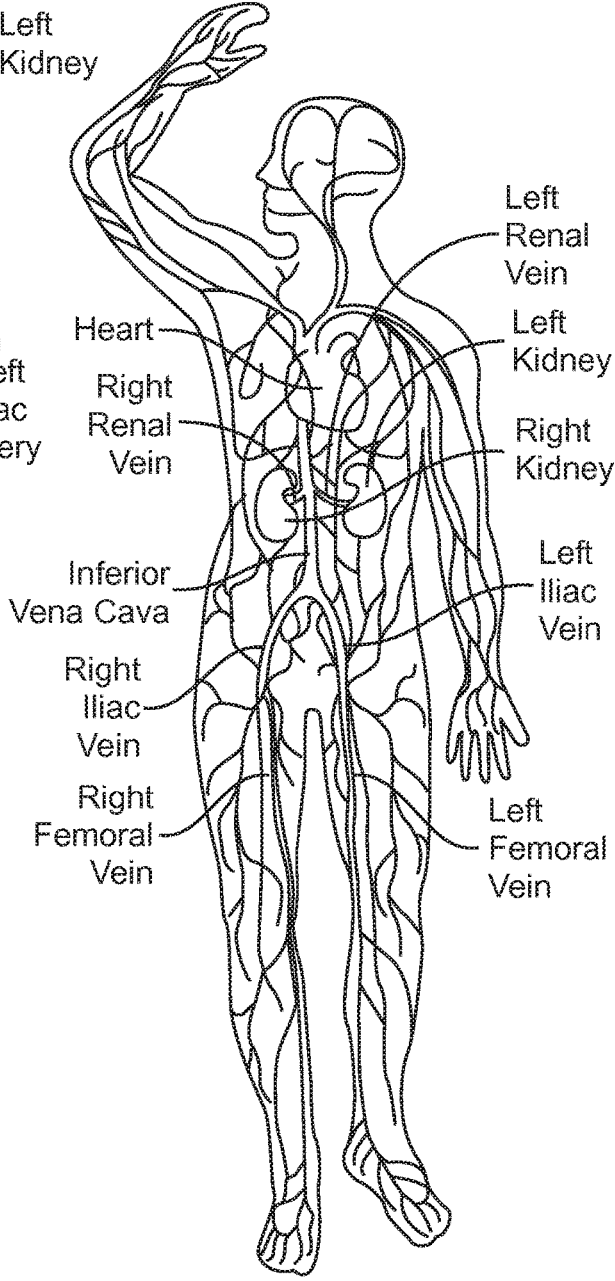

As FIG. 9B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial, to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

Additional Examples

1. A neuromodulation device, comprising:
an elongated shaft having a distal end portion and a mandrel extending at least along the distal end portion;
a transition member having a proximal portion, a distal portion, and a guide wire lumen extending through the proximal and distal portions, and
a neuromodulation assembly coupled to the transition member,
wherein the neuromodulation assembly extends distally from the distal portion of the transition member, and wherein the mandrel extends proximally from the proximal portion of the transition member.

2. The neuromodulation device of example 1 wherein the mandrel is attached to the proximal portion of the transition member.

3. The neuromodulation device of example 1 wherein the mandrel extends through at least a portion of the transition member.

4. The neuromodulation device of example 1 wherein the mandrel extends through the transition member and is attached to the distal portion of the transition member.

5. The neuromodulation device of any one of examples 1-4 wherein the transition member comprises a braided material.

6. The neuromodulation device of any one of examples 1-5 wherein the mandrel has a generally constant outer diameter from a distal end of the mandrel to a proximal end of the mandrel.

7. The neuromodulation device of any one of examples 1-5 wherein the mandrel has a proximal end and a distal end, and wherein the mandrel is tapered from a larger outer diameter at the proximal end to a smaller outer diameter at the distal end.

8. The neuromodulation device of any one of examples 1-5 wherein the mandrel includes a plurality of stepped longitudinal segments, and wherein the stepped longitudinal segments have progressively larger outer diameters as the mandrel extends proximally away from the neuromodulation assembly.

9. The neuromodulation device of any one of examples 1-8 wherein the mandrel comprises a heat treated longitudinal segment, and wherein the heat treated longitudinal segment is less resistant to deflection in response to lateral force than non-heat treated longitudinal segments of the mandrel.

10. The neuromodulation device of any one of examples 1-9 wherein the shaft has a proximal end portion, and wherein the mandrel extends from the distal end portion to the proximal end portion.

11. The neuromodulation device of any one of examples 1-10 wherein the mandrel has an outer diameter of about 0.051-0.071 cm.

12. The neuromodulation device of any one of examples 1-11 wherein the guide wire channel is configured to receive a guide wire for rapid-exchange guide wire procedures.

13. The neuromodulation device of any one of examples 1-12, further comprising:
at least one energy delivery wire extending along the mandrel and operably coupled to the neuromodulation assembly; and
an outer covering encapsulating the elongated shaft, the mandrel, and the at least one energy delivery wire.

14. The neuromodulation device of any one of examples 1-13 wherein the mandrel has an at least substantially solid core.

15. The neuromodulation device of any one of examples 1-14 wherein the mandrel comprises a first longitudinal segment and a second longitudinal segment, wherein the first longitudinal segment has an outer diameter greater than that of the second longitudinal segment, and wherein the first and second longitudinal segments are separated by a tapered zone that has a continuous taper from the outer diameter of the first longitudinal segment to the outer diameter of the second longitudinal segment.

16. A neuromodulation device, comprising:
an elongated shaft having a proximal portion, a distal portion, and a hypotube extending at least along the proximal portion of the shaft, wherein a distal section of the hypotube is flexible at body temperature, and wherein a proximal section of the hypotube is less flexible than the distal section; and
a neuromodulation assembly coupled to the distal, portion of the shaft.

17. The neuromodulation device of example 16 wherein the hypotube is made from nitinol.

18. The neuromodulation device of any one of examples 1-17 wherein the neuromodulation assembly is selectively transformable between a low-profile configuration in a delivery state and an expanded configuration sized to fit within a renal artery in a deployed state.

19. The neuromodulation device of example 18 wherein the neuromodulation assembly has a helical shape in the deployed state.

20. The neuromodulation device of example 19 wherein the neuromodulation assembly comprises one or more energy delivery elements.

71. The neuromodulation device of example 20 wherein the energy delivery elements comprise electrodes.

22. The neuromodulation device of example 19 wherein the neuromodulation assembly comprises a plurality of electrodes.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:
1. A neuromodulation device, comprising:
an elongated shaft having a distal end portion;
a neuromodulation assembly having proximal and distal ends and selectively transformable between a low-profile configuration in a delivery state and an expanded configuration sized to fit within a renal artery in a deployed state, wherein the neuromodulation assembly has a helical shape in the deployed state;

a transition member coupled to the distal end portion of the elongated shaft and to the proximal end of the neuromodulation assembly to form a junction therebetween, the transition member being configured to increase device stability and control at the junction;

a guide wire lumen extending between an opening at the distal end of the neuromodulation assembly and an opening at a proximal portion of the transition member; and a mandrel having a distal end proximal to the neuromodulation assembly, the mandrel bonded to the transition member and extending proximally from the proximal portion of the transition member along at least the distal end portion of the elongated shaft.

2. The neuromodulation device of claim 1 wherein the mandrel is bonded to the proximal portion of the transition member.

3. The neuromodulation device of claim 1 wherein the mandrel extends through at least a portion of the transition member.

4. The neuromodulation device of claim 1 wherein the mandrel extends through the transition member and is bonded to distal portion of the transition member.

5. The neuromodulation device of claim 1 wherein the transition member comprises a braided material.

6. The neuromodulation device of claim 1 wherein the mandrel has a generally constant outer diameter from the distal end of the mandrel to a proximal end of the mandrel.

7. The neuromodulation device of claim 1 wherein the mandrel has a proximal end and the distal end, and wherein the mandrel is tapered from a larger outer diameter at the proximal end to a smaller outer diameter at the distal end.

8. The neuromodulation device of claim 1 wherein the mandrel includes a plurality of stepped longitudinal segments, and wherein the stepped longitudinal segments have progressively larger outer diameters as the mandrel extends proximally away from the neuromodulation assembly.

9. The neuromodulation device of claim 1 wherein the mandrel comprises a first longitudinal segment and a second longitudinal segment, and wherein the first longitudinal segment is less resistant to deflection in response to lateral force than the second longitudinal segment of the mandrel.

10. The neuromodulation device of claim 1 wherein the shaft has a proximal end portion, and wherein the mandrel extends from the distal end portion to the proximal end portion.

11. The neuromodulation device of claim 1 wherein the mandrel has an outer diameter of about 0.051-0.071 cm.

12. The neuromodulation device of claim 1 wherein the guide wire lumen is configured to receive a guide wire for rapid-exchange guide wire procedures.

13. The neuromodulation device of claim 1, further comprising:
   at least one energy delivery wire extending along the mandrel and operably coupled to the neuromodulation assembly; and
   an outer covering encapsulating the elongated shaft, the mandrel, and the at least one energy delivery wire.

14. The neuromodulation device of claim 1 wherein the mandrel has an at least substantially solid core.

15. The neuromodulation device of claim 1 wherein the mandrel comprises a first longitudinal segment and a second longitudinal segment, wherein the first longitudinal segment has an outer diameter greater than that of the second longitudinal segment, and wherein the first and second longitudinal segments are separated by a tapered zone that has a continuous taper from the outer diameter of the first longitudinal segment to the outer diameter of the second longitudinal segment.

16. The neuromodulation device of claim 1 wherein the neuromodulation assembly comprises a plurality of electrodes.

17. The neuromodulation device of claim 1 wherein the neuromodulation assembly comprises one or more energy delivery elements.

18. The neuromodulation device of claim 17 wherein the energy delivery elements comprise electrodes.

* * * * *